(12) United States Patent
Lane et al.

(10) Patent No.: US 7,083,983 B2
(45) Date of Patent: *Aug. 1, 2006

(54) INHIBITORS OF THE INTERACTION BETWEEN P53 AND MDM2

(75) Inventors: David Philip Lane, Fife (GB); Volker Böttger, Germering-Unterpfaffenhofen (DE); Angelika Böttger, Germering-Unterpfaffenhofen (DE); Steven Michael Picksley, Bradford (GB); Heinz-Kurt Hochkeppel, Aesch (CH); Carlos Garcia-Echeverria, Basel (CH); Patrick Chène, Mulhouse (FR); Pascal Furet, Thann (FR)

(73) Assignee: Cancer Research Campaign Technology Limited (CH)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/214,371

(22) PCT Filed: Jul. 4, 1997

(86) PCT No.: PCT/EP97/03549

§ 371 (c)(1),
(2), (4) Date: Mar. 26, 1999

(87) PCT Pub. No.: WO98/01467

PCT Pub. Date: Jan. 15, 1998

(65) Prior Publication Data

US 2001/0018511 A1 Aug. 30, 2001

(30) Foreign Application Priority Data

Jul. 5, 1996 (GB) ................................. 9614197.3
Apr. 7, 1997 (GB) ................................. 9707041.1

(51) Int. Cl.
*G01N 33/566* (2006.01)
*G01N 33/53* (2006.01)
*A61K 38/00* (2006.01)
*A61K 38/12* (2006.01)
*A61K 51/00* (2006.01)

(52) U.S. Cl. .................... 436/501; 424/1.41; 424/1.69; 435/7.1; 530/300; 530/317; 530/328

(58) Field of Classification Search ................. 435/7.1; 424/1.17, 1.41, 1.69; 436/501; 530/300, 530/317, 328, 350; 514/1, 2
See application file for complete search history.

(56) References Cited

U.S. PATENT DOCUMENTS

| 5,362,623 A | 11/1994 | Vogelstein et al. ............. 435/6 |
| 5,411,860 A | 5/1995 | Vogelstein et al. |
| 5,420,263 A * | 5/1995 | Burrell et al. ............. 536/23.1 |
| 5,519,118 A | 5/1996 | Vogelstein et al. |
| 5,532,348 A | 7/1996 | Huibregtse et al. |
| 5,550,023 A | 8/1996 | Kinzler et al. |
| 5,606,044 A | 2/1997 | Burrell et al. |
| 5,618,921 A | 4/1997 | Burrell et al. |
| 5,702,908 A * | 12/1997 | Picksley et al. ............. 435/7.8 |
| 5,770,377 A * | 6/1998 | Picksley et al. ............. 435/7.1 |
| 6,051,384 A | 4/2000 | Zentgraf et al. ............. 435/7.1 |
| 6,121,238 A * | 9/2000 | Dower et al. ................. 514/13 |
| 6,153,391 A | 11/2000 | Picksley et al. |

FOREIGN PATENT DOCUMENTS

| WO | WO 93 20238 | 10/1993 |
| WO | WO 94/00601 | 1/1994 |
| WO | WO 95 07934 | 3/1995 |
| WO | WO 96 02642 | 2/1996 |
| WO | WO 98/01467 | 1/1998 |
| WO | WO 98/13064 | 4/1998 |

OTHER PUBLICATIONS

Report and recommendations of the pane to assess the NIH investment in research on gene therapy. Orkin and Motulsky, co chairs. National Institutes of Health (Dec. 1995).*
Crystal, R. G. Transfer of genes to humans: Early lessons and obstacles to success. Science 270: 404-410 (Oct. 1995).*
Rojanasakul, Y. Antisense oligonucleotide therapeutics: Drug deliver and targeting. Adv. Drug Delivery Rev. 18: 115-131 (1996).*
Stull et al. Antigene, ribozyme and aptamer nucleic acid drugs: Progress and prospects. Pharm. Res. 12:465-483 (Apr. 1995).*

(Continued)

*Primary Examiner*—Jane Zara
(74) *Attorney, Agent, or Firm*—Ginger R. Dreger; Heller Ehrman LLP

(57) ABSTRACT

The present invention relates to compounds capable of binding to the oncogene protein MDM2, processes for the preparation of such compounds, pharmaceutical preparations comprising such compounds, and uses of said compounds, e.g. in the therapeutic (including prophylactic) treatment of an animal or especially of the human body. The present further relates to methods of and compounds for inhibiting the growth of tumor cells which comprise the wild type p53 suppressor by interfering with the interaction between human p53 and human MDM2.

15 Claims, No Drawings

OTHER PUBLICATIONS

Parsons, J.A., Ed. Peptide Hormones. Univ. Park Press, Baltimore (1976).*

Lee, H. et al. Gene vol. 184: 177-183 (1997).*

Bottger, V. et al., Oncogene, vol. 13, pp. 2141-2147 (1996).*

Elliott,G. et al., Cell, vol. 88, pp. 223-233 (1997).*

Derossi, D. et al., J. Biol. Chem., vol. 289, No. 14, pp. 10,444-10,450 (1994).*

Pooga, M. et al., FASEB J., vol. 12, pp. 67-77 (1998).*

Ball K. et al., Current Biology, vol. 7 (1), "Cell-cycle arrest and inhibition of Cdk4 activity by small peptides based on the carboxy-terminal domain of p21$^{WAF1}$," pp. 71-80 (1996).

Blaydes J. et al., Oncogene, vol. 14, "Tolerance of high levels of wild-type p53 in transformed epithelial cells dependent on auto-regulation by mdm-2," pp. 1859-1868 (1997).

Blommers M.J.J. et al., J. Am. Chem. Soc., vol. 119 (14), "On the Interaction Between p53 and MDM2: Transfer NOE Study of a p53-Derived Peptide Ligated to MDM2," pp. 3425-3426 (1997).

Böttger A. et al., J. Mol. Biol., vol. 269, "Molecular Characterization of the hdm2-p53 Interaction," pp. 744-756 (1997).

Böttger V. et al., Oncogene, vol. 18, "Comparative study of the p53-mdm2 and p53-MDMX interfaces," pp. 189-199 (1999).

Böttger V. et al., Oncogene, vol. 13, "Identification of novel mdm2 binding peptides by phage display," pp. 2141-2147 (1996).

Chorev M. and Goodman M., Acc. Chem. Res., vol. 26, "A Dozen Years of Retro-Inverso Peptidomimetics," pp. 266-273 (1993).

Derossi D. et al., J. of Biol. Chem., vol. 269 (14), "The Third Helix of the Antennapedia Homeodomain Translocates through Biological Membranes," pp. 10444-10450 (1994).

Gannon J. et al., Oncogene, vol. 9 (5), "Activating mutations in p53 produce a common conformational effect. A monoclonal antibody specific for the mutant form," pp. 1595-1602 (1990).

Lane D., Exp. Opin. Ther. Patents, vol. 6 (8), "Patent Evaluation—Oncologic, Endocrine & Metabolic—Interruption of binding of MDM-2 and p53 protein; potential for the treatment of cancer," pp. 805-809 (1996).

Lee H. et al., J. Bacteriol., vol. 173 (17), "Molecular Characterization of nosA, a *Pseudomonas stutzeri* Gene Encoding an Outer Membrane Protein Required to Make Copper-Containing N$_2$0 Reductase," pp. 5406-5413 (1991).

Lin J. et al., Genes & Devel., vol. 8 (10), "Several hydrophobic amino acids in the p52 amino-terminal domain are required for transcriptional activation, binding to mdm-2 and the adenovirus 5 E1B 55-kD protein," pp. 1235-1246 (1994).

Lin Y-Z et al., J. of Biol. Chem., vol. 270 (24), "Inhibition of Nuclear Translocation of Transcription Factor NF-κB by a Synthetic Peptide Containing a Cell Membrane-permeable Motif and Nuclear Localization Sequence," pp. 14255-14258 (1995).

Momand J. et al., Cell, vol. 69, "The mdm-2 Oncogene Product Forms a Complex with the p53 Protein and Inhibits p53-Mediated Transactivation," pp. 1237-1245 (1992).

Mundt M. et al., "The tumor suppressor p53 as a target for tumor therapy: An *In vitro* transcription system as an indicator of active p53," Abstract of presentation at University of Dundee, Dundee, Scotland, Jul. 5-9, 1996.

Olson D. et al., Oncogene, vol. 8, "Identification and characterization of multiple mdm-2 proteins and mdm-2-p53 protein complexes," pp. 2353-2360 (1993).

Phelan J.C. et al., J. of Amer. Chem. Soc., vol. 119 (3), "A General Method for Constraining Short Peptides to an α-Helical Conformation," pp. 455-460 (1997).

Picksley S. et al., Oncogene, vol. 9, "Immunochemical analysis of the interaction of p53 with MDM2;—fine mapping of the MDM2 binding site on p53 using synthetic peptides," pp. 2523-2529 (1994).

Picksley S. and Lane D., Current Opinion in Cell Biology, vol. 6, "p53 and Rb: their cellular roles," pp. 853-858 (1994).

Wallace C. Current Opinion in Biotechnology, vol. 6, "Peptide ligation and semisynthesis," pp. 403-410 (1995).

Barak, Y. et al., "mdm2 expression is inducted by wild type p53 activity," EMBO J., 12(2): 461-468, Feb. 1993.

Barak Y & Oren M., "Enhanced binding of a 95 kDa protein to p53 in cells undergoing p-53- mediated growth arrest," EMBO J., 11(6):2115-2121, Jun. 1992.

Böttger A. et al., "Design of a synthetic Mdm2-binding mini protein that activates the p53 response *in vivo*," Curr. Biol. 7:860-869, Oct. 1997.

Brown D.R. et al., "The tumor suppressor p53 and the oncoprotein simian virus 4D T antigen bind to overlapping domains on the MDM2 protein," Mol. Cell. Biol., 13(11): 6849-6857, Nov. 1993.

Cahilly-Snyder L. et al., "Molecular analysis and chromosomal mapping of amplified genes isolated from a transformed mouse 3T3 cell line," Somatic Cell Mol: Genet., 13 (3): 235-244, May 1987.

Chen C.Y. et al., "Interactions between p53 and MDM2 in a mammalian cell cycle checkpoint pathway," PNAS USA, 91(7): 2684-2688, Mar. 1994.

Chen J. et al., "Mapping of the p53 and mdm-2 interaction domains," Mol. Cell Biol., 13: 4107-4114, Jul. 1993.

Colas P. et al., "Genetic selection of peptide aptamers that recognize and inhibit cyclin-dependent kinase 2," Nature, 380: 548-550, Apr. 1996.

Deffie A. et al., "The tumor suppressor p53 regulates its own transcription," Mol. Cell. Biol., 13: 3415-3423, Jun. 1993.

Dyson N. et al., "Adenovirus E1A makes two distinct contacts with the retinoblastoma protein," J. Virology, 66; 4606-4611, Jul. 1992.

Dyson N. et al., "Homologus sequences in adenovirus E1A and human papillomavirus E7 proteins mediate interaction with the same set of cellular proteins," J. Virology, 66: 6893-6902, Dec. 1992.

Farmer G. et al., "Wild-type p53 activates transcription *in vitro*," Nature, 358: 83-86, Jul. 1992.

Finlay, C.A., "The mdm-2 Oncogene can overcome wild-type p53 suppression of transformed cell growth," Mol. Cell. Biol., 13(1): 301-306, Jan. 1993.

Florenes V.A. et al., "MDM2 gene amplification and transcript levels in human sarcomas: Relationship to TP53 gene status," J. Nat. Cancer Institute, 86(17): 1297-1302, Sep. 1994.

Funk W. D. et al., "A transcriptionally active DNA-binding site for human p53 protein complexes," Mol. Cell. Biol., 12(6): 2866-2871, Jun. 1992.

Garcia-Echeverria C. et al., "Structure activity studies of peptide inhibitors of the p53-HDM2 interaction," 15$^{th}$ American Peptide Symposium, Jan. 1997.

Haupt Y. et al., "Cell type-specific inhibition of p53-mediated apoptosis by mdm2," EMBO J., 15(7): 1596-1606, Apr. 1996.

Hupp T.R. et al., "Small peptides activate the latent sequence-specific DNA binding function of p53," Cell, 83: 237-245, Oct. 1995.

Jones S.N. et al., "Rescue of embryonic lethality in Mdm-1deficient mice by absence of p53," Nature, 378: 206-208, Nov. 1995.

Juven T. et al., "Wild type p53 can mediate sequence-specific transactivation of an internal promoter within the mdm2 gene," Oncogene, 8(12): 3411-3416, Dec. 1993.

Kern S.E. et al., "Oncogenic forms of p53 inhibit p53-regulated gene expression," Science, 256: 827-830, May 1992.

Kovar H. et al., "Narrow spectrum of infrequent p53 mutations and absence of MDM2 amplification in Ewing tumours," Oncogene, 8(10): 2683-90, Oct. 1993.

Kussie P.H. et al., "Structure of the MDM2 oncoprotein bound to the p53 tumor suppressor transactivation domain," Science, 274: 948-953, Nov. 1996.

LaVallie E.R. et al., "A thioredoxin gene fusion expression system the *E. coli* cytoplasm," Biotechnology, 11(2): 187-193, Feb. 1993.

Lane D. et al., "On the regulation of the p53 tumour suppressor, and its role in the cellular response to DNA damage," Phil. Trans. R. Soc. Lond. B, 347: 83-87, 1995.

Lees-Miller S.P. et al., "Human DNA-activated protein kinase phosphorylates serines 15 and 37 in the amino-terminal transactivation domain of human p53," Mol. Cell Biol., 12(11):5041-5049, Nov. 1992.

Lin J. et al., "Functions of the p53 protein in growth regulation and tumor suppression," Cold Spring Harbor Symposia on Qualitative Biology, LIX: 215-223, 1994.

Lin Y & Green M., "Similarities between prokaryotic and eukaryotic cyclic AMP-responsive promoter elements," Nature, 340: 656-659, Aug. 1989.

Liu X. et al., "The p53 activation domain binds the TATA box-binding polypeptide in holo-TFIID, and a neighboring p53 domain inhibits transcription," Mol. Cell. Biol., 13; 3291-3300, Jun. 1993.

Lu X. & Lane D., "Differential induction of transcriptionally active p53 following UV and □onizing radiation: Defects in chromosome instability syndromes?," Cell, 75: 765-778, Nov. 1993.

Martin K. et al., "Stimulation of E2F1/DP1 transcriptional activity by MDM2 oncoprotein," Nature, 375: 691-698, Jun. 1995.

Marston N.J. et al., "Interaction of p53 with MDM2 is independent of E6 and does not mediate wild type transformation suppressor function," Oncogene, 9: 2707-2716, Sep. 1994.

Michalovita D. et al., "Conditional inhibition of transformation and of cell proliferation by a temperature-sensitive mutant of p53," Cell, 62: 671-680, Aug. 1990.

Midgley C.A. et al., "Analysis of p53 expression in human tumours: an antibody raised against human p53 expressed in *Esherichia coli*," J. Cell Science, 101(1): 183-189, Jan. 1992.

Montes de Oca Luna R. et al., "Rescue of early emryonic lethality in mdm1-deficient," Nature, 378: 203-206, Nov. 1995.

Oliner J.D. et al., "Amplification of a gene encoding a p53-associated protein in human sarcomas," Nature, 358: 80-83, Jul. 1992.

Oliner J.D. et al., "Oncoprotein MDM1 conceals the activation domain of tumour suppressor p53," Nature, 362: 857-860, Apr. 1993.

Otto A. & Deppert W, "Upregulation of mdm-2 expression in meth a tumor cells tolerating wild-type p53," Oncogene, 8(9): 2591-2603, Sep. 1993.

Picksley S. & Lane D., "The p53-mdm2 autoregulatory feedback loop: a paradigm for the regulation of growth control by p53," BioEssays, 15(10): 689-699, Oct. 1993.

Renzing J. & Lane D., "p53-dependent growth arrest following calcium phosphate-mediated transfection of murine fibroblasts," Oncogene, 10(9): 1865-1868, May 1995.

Schlaeppi J.-M. et al., "Identification of specific hdm2 binding peptides by affinity selection and mass spectrometry," 17th International Congress of Biochemistry and Molecular Biology, San Francisco, USA, Aug. 1997.

Schlichtholz B. et al., "The immune response to p53 in breast cancer patients is directed against immunodominant epitopes unrelated to the mutational hot spot," Cancer Res., 52: 6380-6384, Nov. 1992.

Stephen C.W. et al., "Characterisation of epitopes on human p53 using phage displayed peptide libraries: Insights into antibody-peptide interactions," J. Mol. Biol., 248(1): 58-78, Apr. 1995.

Unger T. et al., "P53: a transdominant regulator of transcription whose function is ablated my mutations occurring in human cancer," EMBO J., 11(4): 1383-1390, Apr. 1992.

Vojtesek B. & Lane D., "Regulation of p53 protein expression in human breast cancer cell lines," J. Cell Science, 105(3): 607-612, Jul. 1993.

Wasylyk C. et al., "P53 mediated death of cells overexpressing MDM2 by an inhibitor of MDM2 interaction with p53," Oncogene 18: 1921-1934, Mar. 1999.

Wu X. et al., "The p53-mdm-2 autoregulatory feedback loop," Genes & Dev., 7: 1126-1132, Jul. 1993.

Koster, et al., "Role for the outer membrane ferric siderophore receptor PupB in signal transduction across the bacterial cell envelope", The EMBO Journal, vol. 13, No. 12, pp. 2805-2813, 1994.

* cited by examiner

SEQUENCE LISTING

```
<160> NUMBER OF SEQ ID NOS:  83

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence:peptide

<400> SEQUENCE: 1

Pro Leu Ser Gln Gln Thr Phe Ser Asp Leu Trp Lys Leu Leu Pro Glu
 1               5                  10                  15

Asn Asn Val

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:peptide
<223> OTHER INFORMATION: Where Xaa may be any amino acid

<400> SEQUENCE: 2

Phe Xaa Xaa Leu Trp
 1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:peptide
<223> OTHER INFORMATION: Xaa represents any amino acid and proline,
      phenylalanine, aspartic acid, tyrosine ,
      tryptophan and leucine are L-amino acids

<400> SEQUENCE: 3

Pro Xaa Phe Xaa Asp Tyr Trp Xaa Xaa Leu
 1               5                  10

<210> SEQ ID NO 4
<211> LENGTH: 10
```

```
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x=proline, leucine, glutamic acid, cysteine or
      glutamine
<221> NAME/KEY: VARIANT
<222> LOCATION: (5)
<223> OTHER INFORMATION: x = arginine, histidine, glutamic acid,
      cysteine, serine or preferably aspartic acid.
<221> NAME/KEY: VARIANT
<222> LOCATION: (6)
<223> OTHER INFORMATION: x = histidine, phenylalanine, or preferably
      tyrosine
<221> NAME/KEY: VARIANT
<222> LOCATION: (10)
<223> OTHER INFORMATION: x=phenylalanine, glutamine or preferably
      leucine
<223> OTHER INFORMATION: Xaa at position 2, 4, 8 and 9 is any amino acid

<400> SEQUENCE: 4

Xaa Xaa Phe Xaa Xaa Xaa Trp Xaa Xaa Xaa
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = proline, leucine, glutamic acid, cysteine
      or glutamine
<221> NAME/KEY: VARIANT
<222> LOCATION: (2)
<223> OTHER INFORMATION: x = arginine, asparagine, alanine, threonine or
      valine
<221> NAME/KEY: VARIANT
<222> LOCATION: (4)
<223> OTHER INFORMATION: X = methionine, isoleucine, threonine,
      arginine, alanine or serine
<221> NAME/KEY: VARIANT
<222> LOCATION: (5)
<223> OTHER INFORMATION: X= arginine, histidine, glutamic acid,
      cysteine, serine or preferably aspartic acid.
<221> NAME/KEY: VARIANT
<222> LOCATION: (6)
<223> OTHER INFORMATION: X = histidine, phenylalanine or preferably
      tyrosine
<221> NAME/KEY: VARIANT
<222> LOCATION: (8)
<223> OTHER INFORMATION: X = glutamic acid, threonine, alanine,
      phenylalanine or serine
<221> NAME/KEY: VARIANT
<222> LOCATION: (9)
<223> OTHER INFORMATION: X= glycine, glutamine, threonine, alanine or
      aspartic acid
<221> NAME/KEY: VARIANT
<222> LOCATION: (10)
<223> OTHER INFORMATION: Xaa = phenylalanine, glutamine or preferably
      leucine

<400> SEQUENCE: 5

Xaa Xaa Phe Xaa Xaa Xaa Trp Xaa Xaa Xaa
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence:peptide
```

```
<400> SEQUENCE: 6

Met Pro Arg Phe Met Asp Tyr Trp Glu Gly Leu Asn
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence:peptide

<400> SEQUENCE: 7

Gln Pro Thr Phe Ser Asp Tyr Trp Lys Leu Leu Pro
  1               5                  10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:peptide

<400> SEQUENCE: 8

Pro Arg Pro Ala Leu Val Phe Ala Asp Tyr Trp Glu Thr Leu Tyr
  1               5                  10                  15

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence:peptide

<400> SEQUENCE: 9

Met Pro Arg Phe Met Asp Tyr Trp Glu Gly Leu Asn Arg Gln Ile Lys
  1               5                  10                  15

Ile Trp Phe Gln Asn Arg Arg Met Lys Trp Lys Lys
             20                  25

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (2)
<223> OTHER INFORMATION: X = methionine, isoleucine, threonine,
      arginine, alanine or serine, preferably methionine
<221> NAME/KEY: VARIANT
<222> LOCATION: (3)
<223> OTHER INFORMATION: X = arginine, histidine, glutamic acid,
      cysteine, serine, or preferably aspartic acid.
<221> NAME/KEY: VARIANT
<222> LOCATION: (4)
<223> OTHER INFORMATION: X = histidine, phenylalanine, or preferably
      tyrosine
<221> NAME/KEY: VARIANT
<222> LOCATION: (6)
<223> OTHER INFORMATION: X = glutamic acid, threonine, alanine,
      phenylalanine or serine, preferably glutamic acid
<221> NAME/KEY: VARIANT
<222> LOCATION: (7)
<223> OTHER INFORMATION: X = glycine, glutamine, threonine, alanine or
      aspartic acid, preferably glycine.
<221> NAME/KEY: VARIANT
<222> LOCATION: (8)
<223> OTHER INFORMATION: X = phenylalanine, glutamine or preferably
      leucine.
```

```
<400> SEQUENCE: 10

Phe Xaa Xaa Xaa Trp Xaa Xaa Xaa
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = arginine, asparagine, alanine, threonine or
      valine, particularly arginine.
<221> NAME/KEY: VARIANT
<222> LOCATION: (3)
<223> OTHER INFORMATION: X = methionine, isoleucine, threonine,
      arginine, alanine or serine, preferably methionine
<221> NAME/KEY: VARIANT
<222> LOCATION: (4)
<223> OTHER INFORMATION: X = arginine, histidine, glutamic acid,
      cysteine, serine or preferably aspartic acid.
<221> NAME/KEY: VARIANT
<222> LOCATION: (5)
<223> OTHER INFORMATION: Xaa = histidine, phenylalanine or preferably
      tyrosine.
<221> NAME/KEY: VARIANT
<222> LOCATION: (7)
<223> OTHER INFORMATION: X = glutamic acid, threonine, alanine,
      phenylalanine or serine, preferably glutamic acid.
<221> NAME/KEY: VARIANT
<222> LOCATION: (8)
<223> OTHER INFORMATION: X = glycine, glutamine, threonine, alanine or
      aspartic acid preferably glycine.
<221> NAME/KEY: VARIANT
<222> LOCATION: (9)
<223> OTHER INFORMATION: X = phenylalanine, glutamine or preferably
      leucine.

<400> SEQUENCE: 11

Xaa Phe Xaa Xaa Xaa Trp Xaa Xaa Xaa
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:peptide

<400> SEQUENCE: 12

Pro Ala Phe Thr His Tyr Trp Pro
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:peptide

<400> SEQUENCE: 13

Pro Thr Phe Ser Asp Tyr Trp Pro
 1               5

<210> SEQ ID NO 14
<211> LENGTH: 8
<212> TYPE: PRT
<213> ORGANISM: Artificial Sequence
<220> FEATURE:
```

```
<223> OTHER INFORMATION: Description of Artificial Sequence:peptide

<400> SEQUENCE: 14

Pro Arg Phe Met Asp Tyr Trp Pro
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:peptide

<400> SEQUENCE: 15

Arg Phe Met Asp Tyr Trp Glu Gly Leu
  1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:peptide

<400> SEQUENCE: 16

Phe Met Asp Tyr Trp Glu Gly Leu
  1               5

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:peptide

<400> SEQUENCE: 17

Gln Glu Thr Phe Ser Asp Leu Trp Lys Leu Leu Pro
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Thr
<221> NAME/KEY: VARIANT
<222> LOCATION: (12)
<223> OTHER INFORMATION: X = Phe-NH2

<400> SEQUENCE: 18

Xaa Gly Pro Ala Phe Thr His Tyr Trp Ala Thr Xaa
  1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Met
<221> NAME/KEY: VARIANT
<222> LOCATION: (12)
<223> OTHER INFORMATION: X = Asn-NH2
```

```
<400> SEQUENCE: 19

Xaa Pro Arg Phe Met Asp Tyr Trp Glu Gly Leu Xaa
 1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Gln
<221> NAME/KEY: VARIANT
<222> LOCATION: (12)
<223> OTHER INFORMATION: Pro-NH2

<400> SEQUENCE: 20

Xaa Pro Thr Phe Ser Asp Tyr Trp Lys Leu Leu Xaa
 1               5                  10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Pro
<221> NAME/KEY: VARIANT
<222> LOCATION: (8)
<223> OTHER INFORMATION: X = Pro-NH2

<400> SEQUENCE: 21

Xaa Ala Phe Thr His Tyr Trp Xaa
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Pro
<221> NAME/KEY: VARIANT
<222> LOCATION: (8)
<223> OTHER INFORMATION: X = Pro-NH2

<400> SEQUENCE: 22

Xaa Thr Phe Ser Asp Tyr Trp Xaa
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Pro
<221> NAME/KEY: VARIANT
<222> LOCATION: (8)
<223> OTHER INFORMATION: X = Pro-NH2

<400> SEQUENCE: 23

Xaa Arg Phe Met Asp Tyr Trp Xaa
 1               5
```

<210> SEQ ID NO 24
<211> LENGTH: 12
<212> TYPE: PRT
<213> ORGANISM: Artificial Sequence
<220> FEATURE:
<221> NAME/KEY: VARIANT
<222> LOCATION: (1)
<223> OTHER INFORMATION: X = Ac-Gln
<221> NAME/KEY: VARIANT
<222> LOCATION: (12)
<223> OTHER INFORMATION: X = Pro-NH2
<223> OTHER INFORMATION: Description of Artificial Sequence:peptide

<400> SEQUENCE: 24

Xaa Glu Thr Phe Ser Asp Leu Trp Lys Leu Leu Xaa
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: Ac-Gln
<221> NAME/KEY: VARIANT
<222> LOCATION: (12)
<223> OTHER INFORMATION: X = Pro-NH2

<400> SEQUENCE: 25

Xaa Pro Thr Phe Ser Asp Leu Trp Lys Leu Leu Xaa
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Gln
<221> NAME/KEY: VARIANT
<222> LOCATION: (12)
<223> OTHER INFORMATION: X = Pro-NH2

<400> SEQUENCE: 26

Xaa Glu Thr Phe Ser Asp Tyr Trp Lys Leu Leu Xaa
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Val
<221> NAME/KEY: VARIANT
<222> LOCATION: (12)
<223> OTHER INFORMATION: X=Phe-NH2

<400> SEQUENCE: 27

Xaa Gln Asn Phe Ile Asp Tyr Trp Thr Gln Gln Xaa
 1               5                  10

```
<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Ile
<221> NAME/KEY: VARIANT
<222> LOCATION: (15)
<223> OTHER INFORMATION: X = Val-NH2

<400> SEQUENCE: 28

Xaa Asp Arg Ala Pro Thr Phe Arg Asp His Trp Phe Ala Leu Glx
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Pro
<221> NAME/KEY: VARIANT
<222> LOCATION: (15)
<223> OTHER INFORMATION: X = Tyr-NH2

<400> SEQUENCE: 29

Xaa Arg Pro Ala Leu Val Phe Ala Asp Tyr Trp Glu Thr Leu Xaa
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Pro
<221> NAME/KEY: VARIANT
<222> LOCATION: (15)
<223> OTHER INFORMATION: X = His-NH2

<400> SEQUENCE: 30

Xaa Ala Phe Ser Arg Phe Trp Ser Asp Leu Ser Ala Gly Ala Xaa
 1               5                  10                  15

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (12)
<223> OTHER INFORMATION: X = Phe-NH2

<400> SEQUENCE: 31

Thr Gly Pro Ala Phe Thr His Tyr Trp Ala Thr Xaa
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence:peptide
```

```
<221> NAME/KEY: VARIANT
<222> LOCATION: (12)
<223> OTHER INFORMATION: X = Asn-NH2

<400> SEQUENCE: 32

Met Pro Arg Phe Met Asp Tyr Trp Glu Gly Leu Xaa
 1               5                  10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys(Acrld) or Ac-Cys
<221> NAME/KEY: VARIANT
<222> LOCATION: (14)
<223> OTHER INFORMATION: X = Pro-NH2

<400> SEQUENCE: 33

Xaa Gly Gln Pro Thr Phe Ser Asp Tyr Trp Lys Leu Leu Xaa
 1               5                  10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (14)
<223> OTHER INFORMATION: X = Pro-NH2
<221> NAME/KEY: UNSURE
<222> LOCATION: (1)
<223> OTHER INFORMATION: X = Ac-Cys

<400> SEQUENCE: 34

Xaa Gly Gln Pro Thr Phe Ser Asp Tyr Trp Lys Leu Leu Xaa
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys(Acrd)
<221> NAME/KEY: VARIANT
<222> LOCATION: (10)
<223> OTHER INFORMATION: X = Pro-NH2

<400> SEQUENCE: 35

Xaa Gly Pro Thr Phe Ser Asp Leu Trp Xaa
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys
<221> NAME/KEY: VARIANT
<222> LOCATION: (10)
<223> OTHER INFORMATION: x = Pro-NH2
```

```
<400> SEQUENCE: 36

Xaa Gly Pro Thr Phe Ser Asp Leu Trp Xaa
 1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac=Cys(Acrd)
<221> NAME/KEY: VARIANT
<222> LOCATION: (9)
<223> OTHER INFORMATION: X = Pro-NH2

<400> SEQUENCE: 37

Xaa Pro Thr Phe Ser Asp Leu Trp Xaa
 1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Cys
<221> NAME/KEY: VARIANT
<222> LOCATION: (9)
<223> OTHER INFORMATION: X = Pro-NH2

<400> SEQUENCE: 38

Xaa Pro Thr Phe Ser Asp Leu Trp Xaa
 1               5

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Biotin-Ser
<221> NAME/KEY: VARIANT
<222> LOCATION: (16)
<223> OTHER INFORMATION: X = Pro-NH2

<400> SEQUENCE: 39

Xaa Gly Ser Gly Gln Glu Thr Phe Ser Asp Leu Trp Lys Leu Leu Xaa
 1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X =  Biotin-Ser
<221> NAME/KEY: VARIANT
<222> LOCATION: (16)
<223> OTHER INFORMATION: X = Pro-NH2

<400> SEQUENCE: 40
```

```
Xaa Gly Ser Gly Gln Pro Thr Phe Ser Asp Leu Trp Lys Leu Leu Xaa
 1               5                  10                  15
```

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: Biotin-Ser
<221> NAME/KEY: VARIANT
<222> LOCATION: (16)
<223> OTHER INFORMATION: X = Pro-NH2

<400> SEQUENCE: 41

```
Xaa Gly Ser Gly Gln Glu Thr Phe Ser Asp Tyr Trp Lys Leu Leu Xaa
 1               5                  10                  15
```

<210> SEQ ID NO 42
<211> LENGTH: 29
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: Biotin-Ser
<221> NAME/KEY: VARIANT
<222> LOCATION: (29)
<223> OTHER INFORMATION: X = Lys-NH2

<400> SEQUENCE: 42

```
Xaa Met Pro Arg Phe Met Asp Tyr Trp Glu Gly Leu Asn Arg Gln Ile
 1               5                  10                  15
Lys Ile Trp Phe Gln Asn Arg Arg Met Lys Trp Lys Xaa
                20                  25
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence:peptide

<400> SEQUENCE: 43

```
Arg Gln Ile Lys Ile Trp Phe Gln Asn Arg Arg Met Lys Trp Lys Lys
 1               5                  10                  15
```

<210> SEQ ID NO 44
<211> LENGTH: 31
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Ala
<221> NAME/KEY: VARIANT
<222> LOCATION: (17)
<223> OTHER INFORMATION: product = bAla
<221> NAME/KEY: VARIANT
<222> LOCATION: (30)
<223> OTHER INFORMATION: product = bAla
<221> NAME/KEY: VARIANT
<222> LOCATION: (31)
<223> OTHER INFORMATION: X = Lys(Biotin)-NH2

<400> SEQUENCE: 44

```
Xaa Ala Val Ala Leu Leu Pro Ala Val Leu Leu Ala Leu Leu Ala Pro
 1               5                  10                 15

Ala Met Pro Arg Phe Met Asp Tyr Trp Glu Gly Leu Asn Ala Xaa
                 20                  25                 30

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence:peptide

<400> SEQUENCE: 45

Ala Ala Val Ala Leu Leu Pro Ala Val Leu Leu Ala Leu Leu Ala Pro
 1               5                  10                 15

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys
<221> NAME/KEY: VARIANT
<222> LOCATION: (8)
<223> OTHER INFORMATION: X = Cys-NH2

<400> SEQUENCE: 46

Xaa Thr Phe Ser Asp Tyr Trp Xaa
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys
<221> NAME/KEY: VARIANT
<222> LOCATION: (8)
<223> OTHER INFORMATION: X = Cys-NH2

<400> SEQUENCE: 47

Xaa Thr Phe Ser Asp Tyr Trp Xaa
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Cys
<221> NAME/KEY: VARIANT
<222> LOCATION: (8)
<223> OTHER INFORMATION: X = Cys-NH2

<400> SEQUENCE: 48

Xaa Ala Phe Thr His Tyr Trp Xaa
 1               5

<210> SEQ ID NO 49
<211> LENGTH: 8
```

```
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys
<221> NAME/KEY: VARIANT
<222> LOCATION: (8)
<223> OTHER INFORMATION: X = Cys-NH2

<400> SEQUENCE: 49

Xaa Ala Phe Thr His Tyr Trp Xaa
 1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Cys
<221> NAME/KEY: VARIANT
<222> LOCATION: (8)
<223> OTHER INFORMATION: X = Cys-NH2

<400> SEQUENCE: 50

Xaa Arg Phe Met Asp Tyr Trp Xaa
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Cys
<221> NAME/KEY: VARIANT
<222> LOCATION: (8)
<223> OTHER INFORMATION: X = Cys-NH2

<400> SEQUENCE: 51

Xaa Arg Phe Met Asp Tyr Trp Xaa
 1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Glu
<221> NAME/KEY: VARIANT
<222> LOCATION: (8)
<223> OTHER INFORMATION: X = Lys-NH2

<400> SEQUENCE: 52

Xaa Thr Phe Ser Asp Tyr Trp Xaa
 1               5

<210> SEQ ID NO 53
<211> LENGTH: 8
<212> TYPE: PRT
<213> ORGANISM: Artificial Sequence
<220> FEATURE:
```

```
<223> OTHER INFORMATION: Description of Artificial Sequence:peptide
<221> NAME/KEY: VARIANT
<222> LOCATION: (1)
<223> OTHER INFORMATION: X = CO-NH bridge (lactam peptide derivative)
<221> NAME/KEY: VARIANT
<222> LOCATION: (1)
<223> OTHER INFORMATION: X = Ac-Glu
<221> NAME/KEY: VARIANT
<222> LOCATION: (8)
<223> OTHER INFORMATION: X = CO-NH bridge (lactam peptide derivative)
<221> NAME/KEY: VARIANT
<222> LOCATION: (8)
<223> OTHER INFORMATION: X = Lys-NH2

<400> SEQUENCE: 53

Xaa Arg Phe Met Asp Tyr Trp Xaa
 1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Phe
<221> NAME/KEY: VARIANT
<222> LOCATION: (3)
<223> OTHER INFORMATION: Product = Aib
<221> NAME/KEY: VARIANT
<222> LOCATION: (6)
<223> OTHER INFORMATION: Product = Aib
<221> NAME/KEY: VARIANT
<222> LOCATION: (8)
<223> OTHER INFORMATION: X = Leu-NH2

<400> SEQUENCE: 54

Xaa Met Xaa Tyr Trp Xaa Gly Xaa
 1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Arg
<221> NAME/KEY: VARIANT
<222> LOCATION: (4)
<223> OTHER INFORMATION: Product = Aib
<221> NAME/KEY: VARIANT
<222> LOCATION: (7)
<223> OTHER INFORMATION: Product = Aib
<221> NAME/KEY: VARIANT
<222> LOCATION: (9)
<223> OTHER INFORMATION: X = Leu-NH2

<400> SEQUENCE: 55

Xaa Phe Met Xaa Tyr Trp Xaa Gly Xaa
 1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Arg
```

```
<221> NAME/KEY: VARIANT
<222> LOCATION: (4)
<223> OTHER INFORMATION: Product = Aib
<221> NAME/KEY: VARIANT
<222> LOCATION: (8)
<223> OTHER INFORMATION: X = Ac3c
<221> NAME/KEY: VARIANT
<222> LOCATION: (9)
<223> OTHER INFORMATION: X = Leu-NH2

<400> SEQUENCE: 56

Xaa Phe Met Xaa Tyr Trp Glu Xaa Xaa
 1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Phe
<221> NAME/KEY: VARIANT
<222> LOCATION: (3)
<223> OTHER INFORMATION: Product = Aib
<221> NAME/KEY: VARIANT
<222> LOCATION: (6)
<223> OTHER INFORMATION: Product = Aib
<221> NAME/KEY: VARIANT
<222> LOCATION: (7)
<223> OTHER INFORMATION: X = Ac3c
<221> NAME/KEY: VARIANT
<222> LOCATION: (8)
<223> OTHER INFORMATION: X = Leu-NH2

<400> SEQUENCE: 57

Xaa Met Xaa Tyr Trp Xaa Xaa Xaa
 1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Ac-Phe
<221> NAME/KEY: VARIANT
<222> LOCATION: (3)
<223> OTHER INFORMATION: Product = Aib
<221> NAME/KEY: VARIANT
<222> LOCATION: (7)
<223> OTHER INFORMATION: x = Ac3c
<221> NAME/KEY: VARIANT
<222> LOCATION: (8)
<223> OTHER INFORMATION: x = Leu-NH2

<400> SEQUENCE: 58

Xaa Met Xaa Tyr Trp Gln Xaa Xaa
 1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Arg
<221> NAME/KEY: VARIANT
```

```
<222> LOCATION: (9)
<223> OTHER INFORMATION: X = Leu-NH2

<400> SEQUENCE: 59

Xaa Phe Met Asp Tyr Trp Glu Gly Xaa
 1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Phe
<221> NAME/KEY: VARIANT
<222> LOCATION: (8)
<223> OTHER INFORMATION: x = Leu-NH2

<400> SEQUENCE: 60

Xaa Met Asp Tyr Trp Glu Gly Xaa
 1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Phe
<221> NAME/KEY: VARIANT
<222> LOCATION: (3)
<223> OTHER INFORMATION: product = Aib
<221> NAME/KEY: VARIANT
<222> LOCATION: (8)
<223> OTHER INFORMATION: x = Leu-NH2

<400> SEQUENCE: 61

Xaa Met Xaa Tyr Trp Glu Gly Xaa
 1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: x = Ac-Phe
<221> NAME/KEY: VARIANT
<222> LOCATION: (6)
<223> OTHER INFORMATION: Product = Aib
<221> NAME/KEY: VARIANT
<222> LOCATION: (8)
<223> OTHER INFORMATION: X = Leu-NH2

<400> SEQUENCE: 62

Xaa Met Asp Tyr Trp Xaa Gly Xaa
 1               5

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence:peptide
```

```
<400> SEQUENCE: 63

Val Gln Asn Phe Ile Asp Tyr Trp Thr Gln Gln Phe
  1               5                  10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence:peptide

<400> SEQUENCE: 64

Thr Gly Pro Ala Phe Thr His Tyr Trp Ala Thr Phe
  1               5                  10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence:peptide

<400> SEQUENCE: 65

Ile Asp Arg Ala Pro Thr Phe Arg Asp His Trp Phe Ala Leu
  1               5                  10

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence:peptide

<400> SEQUENCE: 66

Pro Ala Phe Ser Arg Phe Trp Ser Asp Leu Ser Ala Gly Ala His
  1               5                  10                  15

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence:primer DNA

<400> SEQUENCE: 67
gcggatccga tggtgaggag caggcaaatg                               30

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence:primer DNA

<400> SEQUENCE: 68
gcctgcagcc taattcgatg gcgtccctgt aga                           33

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence:primer DNA

<400> SEQUENCE: 69
gcctgcagct agggaaata agttagcaca at                             32
```

```
<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence:primer DNA

<400> SEQUENCE: 70
gcctgcagct aatcttcttc aaatgaatct gt                                 32

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence:primer DNA

<400> SEQUENCE: 71
ggggatcctg aaatttcctt agctgac                                       27

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence:primer DNA

<400> SEQUENCE: 72
gcggatccat ggtgaggagc aggcaaatg                                     29

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence:peptide
<221> NAME/KEY: VARIANT
<222> LOCATION: (1)
<223> OTHER INFORMATION: X = Biotin-Ser

<400> SEQUENCE: 73

Xaa Gly Ser Gly Glu Pro Pro Leu Ser Gln Glu Thr Phe Ser Asp Leu
 1               5                  10                  15

Trp Lys Leu Leu Pro Glu
            20

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence:peptide

<400> SEQUENCE: 74

Pro Pro Leu Ser Gln Glu Thr Phe Ser Asp Leu Trp Lys Leu Leu Pro
 1               5                  10                  15

Glu Asn

<210> SEQ ID NO 75
<211> LENGTH: 57
<212> TYPE: DNA
<213> ORGANISM: Artificial Sequence
<220> FEATURE:
<223> OTHER INFORMATION: Description of Artificial Sequence:primer DNA
```

```
<400> SEQUENCE: 75
gtccgcctct gagtcaggaa acattttcag acctatggaa actacttcct gaaaacg      57

<210> SEQ ID NO 76
<211> LENGTH: 58
<212> TYPE: DNA
<213> ORGANISM: Artificial Sequence
<220> FEATURE:
<223> OTHER INFORMATION: Description of Artificial Sequence:primer DNA

<400> SEQUENCE: 76
gaccgttttc aggaagtagt ttccataggt ctgaaaatg tttcctgact cagaggcg      58

<210> SEQ ID NO 77
<211> LENGTH: 57
<212> TYPE: DNA
<213> ORGANISM: Artificial Sequence
<220> FEATURE:
<223> OTHER INFORMATION: Description of Artificial Sequence:oligomeric
      DNA

<400> SEQUENCE: 77
gtccgcctct gagtcaggaa acattttcag acctatggaa actacttcct gaaaacg      57

<210> SEQ ID NO 78
<211> LENGTH: 57
<212> TYPE: DNA
<213> ORGANISM: Artificial Sequence
<220> FEATURE:
<223> OTHER INFORMATION: Description of Artificial Sequence:oligomeric
      DNA

<400> SEQUENCE: 78
gaccgttttc aggaagtagt ttccataggt ctgaaaatgt ttcctgactc agaggcg      57

<210> SEQ ID NO 79
<211> LENGTH: 57
<212> TYPE: DNA
<213> ORGANISM: Artificial Sequence
<220> FEATURE:
<223> OTHER INFORMATION: Description of Artificial Sequence:oligomeric
      DNA

<400> SEQUENCE: 79
gtccgcctgt gagtatgcct cgttttatgg attattggga gggtcttaat gaaaacg      57

<210> SEQ ID NO 80
<211> LENGTH: 59
<212> TYPE: DNA
<213> ORGANISM: Artificial Sequence
<220> FEATURE:
<223> OTHER INFORMATION: Description of Artificial Sequence:oligomeric
      DNA

<400> SEQUENCE: 80
gaccgttttc attaagaccc tcccaataat ccataaaacg aggcatactc tcagaggcg    59

<210> SEQ ID NO 81
<211> LENGTH: 35
<212> TYPE: DNA
<213> ORGANISM: Artificial Sequence
<220> FEATURE:
<223> OTHER INFORMATION: Description of Artificial Sequence:primer DNA

<400> SEQUENCE: 81
cgggatccac catgggcgat aaaattattc acctg                              35
```

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence:primer DNA

<400> SEQUENCE: 82
ctcgacgcta acctggccta gggaattcc                                   29

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence:peptide,
      amin acid residues 18-23 of human p53

<400> SEQUENCE: 83

Thr Phe Ser Asp Leu Trp
  1               5

INHIBITORS OF THE INTERACTION BETWEEN P53 AND MDM2

This is a U.S. national phase filing of PCT Application No. PCT/EP97/03549, filed on Jul. 4, 1997, which claims priority to United Kingdom applications GB9614197.3 filed on Jul. 5, 1996, and GB9707041.1 filed on Apr. 7, 1997, the disclosures of which are hereby expressly incorporated by reference in their entireties.

The present invention relates to compounds capable of binding to the oncogene protein MDM2, processes for the preparation of such compounds, pharmaceutical preparations comprising such compounds, and uses of said compounds, e.g. in the therapeutic (including prophylactic) treatment of an animal or especially of the human body. The present further relates to methods of and compounds for inhibiting the growth of tumor cells which comprise the wild type p53 suppressor by interfering with the interaction between human p53 and human MDM2.

Inactivation of the p53 tumor suppressor is a frequent event in human neoplasia. Such inactivation of p53 may, for example, result from the binding of a cellular oncogene protein, such as MDM2. The protein encoded by the mdm2 gene, which is also referred to as hdm2 (human double minute 2) gene in the art, is capable of forming a complex with p53 both in vitro and in vivo and inhibit p53-mediated transactivation (J. Momand et al., Cell 69, 1237–1245 (1992)). Formation of this complex favors nucleoplasmic transformation because the complexed p53 essentially looses its tumor suppressor activity. MDM2 is overproduced in about 30% of the human sarcomas and has been associated with an oncogenic phenotype. Compounds preventing or decreasing the binding of MDM2 to p53 alleviate the sequestration of p53, thus promoting p53 tumor suppressor activity. Surprisingly it has been found that the compounds of the invention interfere with the interaction of MDM2 with p53 and activate p53 function and p53 accumulation in normal cells having non-elevated MDM2 levels.

The MDM2 binding site is localized within the region of p53 represented approximately by amino acids 13 to 31 (PLSQETFSDLWKLLPENNV SEQ ID NO:1; single letter code) of mature human p53 protein. Recently, it has been found that peptide fragments of p53 which include the amino acid motif FxxLW SEQ ID NO:2 wherein F, L, and W represent the single letter codes for amino acids phenylalanine, leucine and tryptophan, respectively, and X may be any amino acid, would be particularly suitable for interfering with the binding between p53 and MDM2 (Picksley et al., Oncogene 9, 2523–2529 (1994)). However, there is still a need for compounds which are potent inhibitors of P53-MDM2 binding, and therefore beneficial in the treatment of p53-related diseases, such as (hyper)proliferative diseases. It is the object of the present invention to fulfill this and other needs.

In one aspect, the present invention is based on the surprising finding that a peptide with the phage consensus amino acid sequence P-X-F-X-D-Y-W-X-X-L SEQ ID NO:3, wherein X is any naturally occurring L-amino acid, and P, F, D, W and L represent the L-amino acids of proline (P), phenylalanine (F), aspartic acid (D), tyrosine (Y), tryptophan (W) and leucine (L), respectively, given in the single letter code, is capable of blocking the interaction of MDM2 with p53, as determinable e.g. in an ELISA assay, and shows a significant increase in specific blocking activity over the wildtype p53 peptide sequence.

As used herein, "mdm" refers to the oncogene and "MDM" refers to the protein obtainable as a result of expression of said gene. Even though in the strict sense "mdm" means "murine double minute gene2," as used herein it also refers to dm2 mutants, particularly interspecies mutants, such as hdm2 (human double minute gene2) in particular.

More specifically, it is an object of the present invention to provide compounds capable of interfering with the interaction between p53 and MDM2 and/or mdm2 in tumor cells having wild type p53, particularly human p53, and non-elevated MDM2 levels, as defined below, in vivo and in vitro. A preferred embodiment includes peptides and derivatives thereof, capable of binding to MDM2, particularly human DM2, and specifically exhibiting or blocking the binding of MDM2 to the p53 protein, particularly human p53, in vitro or in vivo. The preferred peptides of the invention are better than the wild type wild type peptide in inhibiting the hdm2 binding to p53 or a suitable p53 peptide, as can be determined e.g. in suitable ELISA-type assays, particularly the assays described in detail hereinafter, on the basis of the $IC_{50}$, i.e. the concentration of peptide necessary to inhibit the hdm2 or p53 binding by 50%. The peptides of the invention mimic the MDM2 binding site on p53. The peptides provided herein consist of or comprise an amino acid motif (in N- or C-terminal order) of the formula $$R_1\text{-}X\text{-}F\text{-}X\text{-}R_2\text{-}R_3\text{-}W\text{-}X\text{-}X\text{-}R_4 \quad \text{(I) SEQ ID NO: 4}$$

wherein $R_1$ is a proline (P), leucine (L), glutamic acid (E), cysteine (C) or glutamine (Q), X stands for one (any) natural amino acid, $R_2$ is arginine (R), histidine (H), glutamic acid (E), cysteine (C), serine (S), or preferably aspartic acid (D), $R_3$ is histidine (H), phenylalanine (F) or preferably tyrosine (Y), $R_4$ is phenylalanine (F), glutamine (Q) or preferably leucine (L); and F and W (as well as the other capital letters given in brackets above) are used in accordance with the commonly used single letter code for amino acids and represent phenylalanine and tryptophan, respectively.

As used herein, the term "amino acid(s)" includes the free (charged or uncharged) form, or the monovalent or bivalent radical, the latter also being referred to as "amino acid residue." For example, in a 10mer peptide of formula (I), $R_1$ and $R_4$ are monovalent radicals, $R_1$ having a free amino group and $R_4$ having a free carboxy group, and X, for example, is a bivalent amino acid radical.

Preferred peptides of the invention consisting of or comprising the amino acid motif of formula (I) are peptides consisting of no more than fifteen amino acids (15mers), particularly 10mer, 11mer, 12mer, 13mer, 14mer or 15mer peptides. In such peptides comprising the amino acid motif of formula (I) natural amino acid residues may be attached to the 10mer motif of formula (I) at the N-terminus, i.e. such additional amino acids precede $R_1$, at the N-terminus; at the C-terminus, i.e. such amino acids follow $R_4$; or at both ends of a peptide of formula (I). Sequences of exemplary 12mer and 15mer peptides are given e.g. in Example 8 hereinbelow.

As used herein, a natural amino acid is a natural α-amino acid having the L-configuration, such as those normally occurring in natural proteins. Unnatural amino acid refers to an amino acid, which normally does not occur in proteins, e.g. an epimer of a natural α-amino acid having the L-configuration, that is to say an amino acid having the unnatural D-configuration; or a (D,L)-isomeric mixture thereof; or a homologue of such an amino acid, for example a β-amino acid, an α-,α-disubstituted amino acid, or an α-amino acid wherein the amino acid side chain has been shortened by one or two methylene groups or lengthened to up to 10 carbon atoms, such as an α-amino alkanoic acid with 5 up to and including 10 carbon atoms in a linear chain, an unsubstituted or substituted aromatic (α-aryl or α-aryl lower alkyl), for example a substituted phenylalanine or phenylglycine.

By selectively disrupting or preventing p53 from binding to MDM2 through its MDM2 binding site, the peptides of the invention, or derivatives thereof, can significantly decrease or avoid the negative regulatory effects of MDM2 on p53 activity. Therefore, the peptides, or derivatives thereof, of the invention can be used to restore p53 tumor suppressor function, e.g. in the treatment of tumor diseases or viral infections when enhanced activity of p53 is desired or required.

The peptide sequences of the invention show some homology to the sequence on p53 required for MDM2 binding, however, additional homologies are present which are absent from p53.

Preferred is a peptide of formula $$R_1\text{-}X_1\text{-}F\text{-}X_2\text{-}R_2\text{-}R_3\text{-}W\text{-}X_3\text{-}X_4\text{-}R_4 \quad \text{(Ia) SEQ ID NO:5,}$$

wherein $R_1$, $R_2$, $R_3$ and $R_4$ each have the meanings given for formula (I) above, $X_1$ is arginine, asparagine, alanine, threonine or valine;

$X_2$ is methionine, isoleucine, threonine, arginine, alanine or serine;

$X_3$ is glutamic acid, threonine, alanine, phenylalanine or serine;

$X_4$ is glycine, glutamine, threonine, alanine or aspartic acid.

In particular, preferred peptides of the invention include the following (amino acid sequences are given in single letter code):

M-P-R-F-M-D-Y-W-E-G-L-N      (II) SEQ ID NO:6;

Q-P-T-F-S-D-Y-W-K-L-L-P      (III) SEQ ID NO:7

P-R-P-A-L-V-F-A-D-Y-W-E-T-L-Y      (IV) SEQ ID NO:8.

As used herein, "peptide of the invention" refers to a linear compound comprising the amino acid motif of formula (I) and containing only natural amino acids which are linked by peptide bonds and which are in an unprotected form.

The present invention also provides derivatives of the peptides of the invention. Such derivatives may be linear or circular. Derivatives of the invention include molecules wherein a peptide of the invention is non-covalently or preferably covalently modified by substitution, chemical, enzymatic or other appropriate means with another atom or moiety including another peptide or protein. An example of a derivative comprising a peptide linked to another protein is exemplified by binding element TIP12/1 as described in example 10 below. The moiety may be "foreign" to a peptide of the invention as defined above in that it is an unnatural amino acid, or in that one or more, preferably one or two natural amino acid in the motif of formula (I) are replaced with another natural or unnatural amino acid. Conjugates comprising a peptide or derivative of the invention covalently attached to another peptide or protein are also encompassed herein. Attachment of another moiety may involve a linker or spacer, e.g. an amino acid or peptidic linker. Derivatives of the invention also includes peptides wherein one, some or all potentially reactive groups, e.g. amino, carboxy, sulfhydryl or hydroxyl groups are in a protected form.

The atom or moiety derivatizing a peptide of the invention may serve analytical purposes, e.g. facilitate detection of the peptide of the invention, favor preparation or purification of the peptide, or improve a property of the peptide which is relevant for the purposes of the present invention. Such properties include e.g. cellular uptake, binding to MDM2, or suitability for in vivo administration, particularly solubility or stability against enzymatic degradation. Derivatives of the invention include a covalent or aggregative conjugate of a peptide of the invention with another chemical moiety, said derivative displaying essentially the same activity as the underivatized peptide of the invention, and a "peptide analogue" or "mimetic" which is modeled to resemble the three-dimensional structure of the amino acid motif of formula (I). Examples of such mimetics are retro-inverso peptides (M. Chorev, M. Goodman, Acc. Chem. Res. 26, 266–273 (1993)). The designing of mimetics to a known pharmaceutically active compound is a known approach to the design of drugs based on a "lead" compound. This may be desirable e.g. where the "original" active compound is difficult or expensive to synthesize, or where it is unsuitable for a particular mode of administration, e.g. peptides are considered unsuitable active agents for oral compositions as they tend to be quickly degraded by proteases in the alimentary channel.

Examples of derivatives within the above general definitions are:

Cyclic peptides or derivatives including compounds with a disulfide bridge, a thioether bridge or a lactam. Typically, cyclic derivatives containing a disulphide bond will contain two cysteines, which may be L-cysteine or D-cysteine. Advantageously, the N-terminal amino acid (e.g. $R_1$ in formula I) and the C-terminal amino acids are both cysteines. In such derivatives, as an alternative to cysteine, penicill amine (β, β-dimethyl-cysteine) can be used. Peptides containing thioether bridges are obtainable e.g. from starting compounds having a free cysteine residue at one end and a bromo-containing building block at the other end (e.g., bromo-acetic acid). Cyclisation can be carried out on solid phase by a selective deprotection of the side chain of cysteine. A cyclic lactam may be formed e.g. between the γ-carboxy group of glutamic acid and the ε-amino group of lysine. For example, cyclic lactams according to the invention have a Glu at the N-terminus (e.g. $R_1$ in formula I) and a Lys at the C-terminus. As an alternative to glutamic acid, it is possible to use aspartic acid. As an alternative to lysine, ornithine or diaminobutyric acid may be employed. Also, it is possible to make a lactam between the side chain of aspartic acid or glutamic acid at the C-terminus and the α-amino acid group of the N-terminal amino acid. This approach is extendable to β-amino acids (e.g., β-alanine). Alternatively, glutamine residues at the N-terminus or C-terminus can be tethered with an alkenedyl chain between the side chain nitrogen atoms (J. C. Phelan et al., J. of the American Chemical Society 119, 455–460 (1997)).

Peptides of the invention, which are modified by substitution. In the sequence of formula (I) one or more, preferably one or two, amino acids are replaced with another natural or unnatural amino acid, e.g. with the respective D-analog, or a mimetic. For example, in a peptide, wherein $R_3$ is Phe or particularly Tyr, Phe or Tyr may be replaced with another building block, e.g. another proteinogenic amino acid, or a structurally related analogue. Preferred modifications are such that an α-helix conformation in the peptide is induced, increased or maintained. For example, in a peptide of formula (I), $R_2$, $X_3$ and/or $X_4$ may, independently from one another, be replaced by a α,α-disubstituted amino acid residue, α-aminoisobutyric acid, 1-amino-cyclopropane-1-carboxylic acid, 1-amino-cyclopetane-1-carboxylic acid, 1-amino-cyclohexane-1-carboxylic acid, 4-amino piperidine-4-carboxylic acid and 1-amino-cycloheptane-1-carboxylic acid.

Peptides of the invention labeled with an enzyme, a fluorescent marker, a chemiluminescent marker, a metal chelate, paramagnetic particles, biotin, or the like. In such derivatives, the peptide of the invention is bound to the conjugation partner directly or by way of a spacer or linker group, e.g. a (peptidic) hydrophilic spacer. Advantageously, the peptide is attached at the N- or C-terminal amino acid. For example, biotin may be attached to the N-terminus of a peptide of the invention via a serine residue or the tetramer SerGlySerGly.

Peptides of the invention carrying one or more protecting groups at a (potentially) reactive (side group), such as amino-protecting group, e.g. acetyl, or a carboxy-protecting group. For example, the C-terminal carboxy group of a compound of the invention may be present in form of a carboxamide function. Suitable protecting groups are commonly known in the art and further exemplified hereinbelow. Such groups may be introduced e.g. to enhance the stability of the compound against proteolytic degradation. If desired, such protecting groups are removed.

Peptides of the invention fused or attached to another protein or peptide, e.g. a protein or peptide serving as internalization vector, such as another peptide facilitating cellular uptake, e.g. a "penetratin." An exemplary penetratin comprising derivative according to the invention is e.g. a peptide comprising the sixteen amino acid sequence from the homeodomain of the Antennapedia protein (E. Derossi et al., J. Biol. Chem. 269, 10444–10450 (1994)), particularly a peptide having the amino acid sequence: M-P-R-F-M-D-Y-W-E-G-L-N-R-Q-I-K-I-W-F-Q-N-R-R-M-K-W-K-K SEQ ID NO:9, or comprising a peptide sequence disclosed by Y. -Z. Lin et al., J. Biol. Chem. 270, 14255–14258 (1995)), Salts, especially acid addition salts, salts with bases or, where several salt-forming groups are present, mixed salts or internal salts. Exemplary salts are e.g. the salts described in the Examples. Preferred are pharmaceutically acceptable salts. However, it is also possible to use pharmaceutically unacceptable salts, e.g. for isolation or purification purposes.

Derivatives of a peptide of the invention also comprise fragments of such peptide which, as compared to a peptide of formula (I), consist of or comprise at least eight i.e. eight or nine, consecutive amino acids of said motif. Such fragments may be further derivatized as described in detail above.

More specifically, a preferred fragment according to the invention is an 8mer peptide, i.e. a peptide containing eight amino acid residues, of formula F-$X_2$-$R_2$-$R_3$-W-$X_3$-$X_4$-$R_4$  (Ib) SEQ ID NO:10, wherein $R_2$, $R_3$ and $R_4$, independently from one another, each have the meanings and preferences given for formula (I) above, $X_2$ is methionine, isoleucine, threonine, arginine, alanine or serine, preferably methionine;

$X_3$ is glutamic acid, threonine, alanine, phenylalanine or serine, preferably glutamic acid;

$X_4$ is glycine, glutamine, threonine, alanine or aspartic acid, preferably glycine, or a derivative as defined above of such fragment.

Also preferred is a fragment, which is a 9mer peptide having the formula $X_1$-F-$X_2$-$R_2$-$R_3$-W-$X_3$-$X_4$-$R_4$  (Ic) SEQ ID NO:11, wherein $R_1$, $R_2$, $R_3$ and $R_4$, independently from one another, each have the meanings and preferences given for formula (I) above, $X_1$ is arginine, asparagine, alanine, threonine or valine; particularly arginine $X_2$ is methionine, isoleucine, threonine, arginine, alanine or serine; preferably methionine;

$X_3$ is glutamic acid, threonine, alanine, phenylalanine or serine; preferably glutamic acid;

$X_4$ is glycine, glutamine, threonine, alanine or aspartic acid, preferably glycine, or a derivative as defined above of such fragment.

Particularly preferred derivatives of peptide fragments of the invention contain the 8mer motif of formula (Ib) or the 9mer motif of formula (Ic) and also
   a suitable label means, e.g. an enzyme, a fluorescent marker, a chemiluminescent marker, a metal chelate, paramagnetic particles, biotin, or the like, and/or
   one or more protecting groups, e.g. as defined above, such as acetyl, and/or
   be fused or attached to another protein or peptide, e.g. a peptide as mentioned above.

Also included within the scope of the provided fragment derivatives are peptides of formula (Ib) or (Ic), wherein one or more, preferably one, two or three amino acid residues are replaced with another natural or unnatural amino acid. For example, in a peptide, wherein $R_3$ is Phe or particularly Tyr, Phe or Tyr may be replaced with another building block, e.g. another proteinogenic amino acid, or a structurally related analogue, e.g. ortho-tyrosine, homophenylalanine or 2-naphtyl-alanine. Preferred modifications are such that an α-helix conformation in the fragment is induced, increased or maintained. For example, in a peptide of formula (I), each of $R_2$, $X_3$ and/or $X_4$ may, independently from one another, be replaced by a α,α-disubstituted amino acid residue, such as α-aminoisobutyric acid (Aib), 1-amino-cyclopropane-1-carboxylic acid, 1-amino-cyclopropane-1-carboxylic acid, 1-amino-cyclopentane-1-carboxylic acid, 1-amino-cyclohexane-1-carboxylic acid, 4-aminopiperidine-4-carboxylic acid, or 1-amino-cycloheptane-1-carboxylic acid. Such replacement may be combined with the above mentioned substitution by ortho-tyrosine. Also, in a 9mer fragment of formula (Ic), wherein $R_2$ is aspartic acid and the remaining variables have the meanings and preferences given above, $X_1$ may be replaced with $NH_2$—$(CH_2)_n$—CO—, wherein n is from 4 to 6, preferably a 6-amino-hexanoic acid residue. The N-terminal amino group of such fragment derivative will form a lactam with the side chain of aspartic acid.

Exemplary fragments include the following: P-A-F-T-H-Y-W-P SEQ ID NO:12, and, particularly, P-T-F-S-D-Y-W-P SEQ ID NO:13 and P-R-F-M-D-Y-W-P SEQ ID NO:14, or derivatives thereof. Particularly preferred are fragments having the following amino acid sequences: R-F-M-D-Y-

W-E-G-L SEQ ID NO:15 and F-M-D-Y-W-E-G-L SEQ ID NO:16, or derivatives thereof.

Specially preferred derivatives of the invention are the derivatives used to exemplify the present invention, derivatives of the peptides above designated as being preferred and derivatives of fragments as defined above.

A derivative according to the invention may involve one or multiple modifications as compared to a peptide of the invention, e.g. carry one or more of the above defined moieties. In other words, a derivative of the invention is intended to include compounds derivable from or based on a peptide of the invention or another derivative of the invention. The preferred derivatives of the invention are capable of binding to MDM2 and of selectively inhibiting or blocking the binding of MDM2 to the p53 protein.

The compounds of the invention have useful, in particular pharmacologically useful properties. For example, they are useful in the treatment of diseases that respond to the inhibition of the p53-MDM2 interaction. As used hereinbefore or hereinbelow, the term "compound of the invention" includes peptides and derivatives of the peptides of the invention as well as DNA encoding for the described peptides and derivatives, triple-strand forming or antisense nucleotides, small molecules or peptides capable of inhibiting expression of MDM2, and antibodies and any further molecules capable of inhibiting p53-MDM2 interaction.

The ability of a test compound to inhibit interaction between MDM2 and p53 can be shown by assays commonly known in the art, or modifications of known assays readily apparent to a person of ordinary skill in the art. Suitable assays include e.g. a binding assay determining binding of a test compound, e.g. a compound of the invention, to MDM2, an in vitro transcription assay or an assay as described in European Patent Application 95810576.9, corresponding to International Application No. PCT/EP 96/03957. Assays may be performed qualitatively or quantitatively and require comparison to one or more suitable controls.

A preferred binding assay is a competitive binding assay. The principle underlying a competitive binding assay is generally known in the art. Briefly, such binding assay is performed by allowing a compound to be tested for its capability to compete with a known, suitably labeled ligand, e.g. MDM2 or p53 for the binding site at a target molecule, e.g. p53 or MDM2 (depending on which molecule is used as known ligand). A suitably labeled ligand is e.g. a radioactively labeled ligand or a ligand which can be detected by its optical properties, such as absorbance or fluorescence. After removing unbound ligand and test compound the amount of labeled ligand bound to the target protein is measured. If the amount of bound ligand is reduced in the presence of the test compound, said compound is found to bind to the target molecule.

Further details of suitable assays are given in the Examples. For example, ELISA-type assays may be used wherein p53 or an appropriately labeled p53 peptide comprising the MDM2 binding site on p53 is immobilized and binding of MDM2 is competed for by a candidate inhibitor. Alternatively, MDM2 may be immobilized and binding of p53 is competed for by such candidate. Furthermore, an assay involving phage display of a candidate peptide, e.g. a phage ELISA assay, may be used.

Particularly preferred compounds of the invention are superior to the peptide having the amino acid sequence QETFSDLWKLLP SEQ ID NO:17 corresponding to the correct p53 wild-type sequence in their ability to selectively inhibit the binding of p53 and MDM2.

The peptides and derivatives of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Reactive derivatives of carbonic or sulfonic acids are preferably reactive esters, reactive anhydrides or reactive cyclic amides. Reactive carbonic acid or reactive sulfonic acid derivatives can also be formed in situ.

The reaction steps required e.g. for the synthesis of amide or sulfonamide bonds usually depend on the type of activation of the carboxylic or sulfo group participating in the reaction. The reactions normally run in the presence of a condensing agent or, when activating the carboxylic or sulfonic acids in the form of anhydrides, of an agent that binds the carboxylic or sulfonic acid formed. The reactions are especially carried out in a temperature range from −30 to +150° C., preferably from +10 to +70° C., and, most preferably, from +20 to +50° C., if appropriate, in an inert gas atmosphere, e.g. under nitrogen or argon.

Synthesis proceeds in a stepwise, cyclical fashion by successively removing the $NH_2$ protecting group of the amino group to be reacted next and then coupling an activated fragment (e.g. an amino acid, di-, tri- or oligopeptide or a carboxylic acid or sulfonic acid, or a reactive derivative thereof, to the deprotected $NH_2$ (e.g. α- or β-$NH_2$). Preferably, activation of the COOH group of the amino acid to be reacted or the carboxyl or sulfo group of the acid to be attached by the condensation reaction is effected (i) directly with a carbodiimide, with a carbonyl compound such as carbonyldiimidazole; with 1,2-oxazolium compounds; with acylamino compounds such as 2-ethoxy-1-ethoxycarbonyl-1,2-dihydroquinoline; with N-[(dimethylamino)-1H-1,2,3-triazolo[4,5-b]pyridin-1-ylmethylene]-N-methylmethanaminium hexafluorophosphate N-oxide (HATU); with an uronium compound such as 2-(1H-benzotriazol-1-yl)-1,1,3,3-tetramethyl-uronium tetrafluoroborate (HBTU); or phosphonium compounds such as benzotriazol-1-yl-oxy-tris(dimethylamino)-phosphonium hexafluoro phosphate (BOP) or benzotriazol-1-yl-oxy-pyrrolidino-phosphonium hexafluorophosphate (PyBOP);

(ii) via formation of the symmetric anhydride (obtainable, for example, by condensation of the corresponding acid in the presence of a carbodiimide or 1-diethyl-aminopropyne; symmetric anhydrides method), or an asymmetric anhydride, such as the respective carbonic or sulfonic acid bromide, chloride or fluoride, or (iii) by formation of an "active ester," e.g. an amino- or amino ester, such as a 1-hydroxy-benzotriazole (HOBT) or N-hydroxysuccinimide ester, or an aryl ester, such as a penta-fluorophenyl, 4-nitrophenyl or 2,4,5-tetrachlorophenyl ester;

or by an appropriate combination of any of the reagents and reactions mentioned under (i) to (iii).

Useful acid binding agents that can be employed in the condensation reactions are, for example, alkaline metals, carbonates or bicarbonates, such as sodium or potassium carbonate or bicarbonate (if appropriate, together with a sulfate), or organic basis such as sterically hindered organic nitrogen bases, for example tri-lower alkylamines, such as N,N-diisopropyl-N-ethylamine, which can be used alone or in any appropriate combination.

Reactive groups in the monomers of ligands or in the resin-bound or free intermediates resulting from one or more coupling steps can be protected by third groups as protecting groups that are customarily used in peptide synthesis. Examples of protecting groups, their introduction and their removal are, for example, described in standard works such as "Protective groups in Organic Chemistry," Plenum Press, London, New York 1973; "Methoden der organischen Chemie," Houben-Weyl, 4. edition, Vol. 15/1, Georg-Thieme Verlag, Stuttgart 1974; Th. W. Greene, "Protective Groups in Organic Synthesis," John Wiley & Sons, New York 1981; Atherton et al., "Solid Phase Peptide Synthesis—A Practical Approach," IRL Press Oxford University, 1984; Jones, "The Chemical Synthesis of Peptides," Oxford Science Publications, Clavendon Press Oxford, 1991; and Bodanszky, "Peptide Chemistry," Springer Verlag Berlin, 1988. The term "protecting groups" comprises also resins used for solid phase synthesis, preferably those specifically mentioned above and below.

Examples for hydroxy protecting groups are acyl radicals, such as tert-lower alkoxycarbonyl radicals, for example tert-butoxycarbonyl, etherifying groups, such as tert-lower alkyl groups, for example t-butyl, or silyl- or tin radicals, such as tert-butyl-dimethylsilyl or the tri-n-butyltin radical.

Carboxy groups can be protected by groups as defined above for the C-terminal protecting groups Y, preferably by esterifying groups selected from those of the tert-butyl type, from benzyl, from trimethylsilylethyl and from 2-triphenyl-silyl groups, or they can be protected as lower aklenyl esters, such as allylic esters.

Amino or guanidine (e.g. in H-Arg-OH) groups can be protected by removable acyl groups or by arylmethyl, etherified mercapto, 2-acyl-lower alk-1-enyl, a silyl group or an organic sulfonyl group or tin amino protecting groups; tert-butoxycarbonyl, allyloxycarbonyl, benzyl-oxycarbonyl, 4-nitrobenzyloxycarbonyl, 2-chlorobenzyloxycarbonyl, 2-bromobenzyloxy-carbonyl, diphenylmethoxycarbonyl, nitrophenylsulfenyl, 2,2,2-trichloro-ethoxycarbonyl, 2,2,5,7,8-pentamethylchroman-6-sulfonyl (PMC—very preferred), 2,2,4,6,7-pentamethyldihydrobenzofuran-5-sulfonyl (Pbf) or 4-methoxy-2,3,6-tri methyl-benzenesulfonyl (Mtr) being especially preferred.

Carbamide groups (for example, in the side chains of asparagine and glutamine) can be protected at the nitrogen atom by arylmethyl groups, preferably triphenylmethyl (trityl) or analogues thereof with one or more lower alkoxy, such as methoxy, and/or lower alkyl, such as methyl, substituents in one or more phenyl rings.

Imino groups (e.g. in imidazole) can be protected by 2,4-dinitrophenyl, trityl, tert-butoxy-carbonyl or p-toluene sulfonyl, or (e.g. in indole) by formyl or tert-butoxycarbonyl.

Mercapto groups can be protected, e.g. by acetamidomethyl, by titryl or by p-methylbenzyl.

A large number of methods of removing protective groups in the fina products or any inter-mediates are known in the art and comprise, inter ali, β-elimination, solvolysis, hydrolysis, alcoholysis, acidolysis, photolysis, enzymatical removal, treatment with a base or reduction.

The protective groups are usually removed after the complete synthesis of the resin-bound molecule by conventional methods of peptide chemistry, conveniently by treatment with 95% trifluoroacetic acid (Fmoc-chemistry). In some cases, strong nucleophiles, such as dimethyl sulfide and/or 2-ethanedithiol, may be additionally added to capture the generated compounds resulting from the protecting groups, e.g. in a combination such as trimethyl-silyltrifluoro-methansulfonate/dimethylsulfide/trifluoroacetic acid/ethanedithiol/m-cresol.

The two preferred methods of solid phase peptide synthesis are the Boc and the Fmoc methods, which are named with reference to their use of the tert-butoxycarbonyl (Boc) or 9-fluorenylmethyloxycarbonyl (Fmoc) group, respectively, to protect the $\alpha$-$NH_2$ or $\alpha$-$NHR_3$ of the amino acid residue to be coupled (see J. M. Stewart, J. D. Young, Solid-Phase Peptide Synthesis, 2n edn., Pierce, Rockford, Ill. (1984) or G. Barany, R. B. Merrifield, Solid-phase Peptide Synthesis, in: The Peptides, Vol. 2 (E. Gross, J. Meienhofer, eds.), Academic Press, New York (1979)); and E. Atherton and R. C. Sheppard, in Solid-Phase Peptide Synthesis—A Practical Approach, ed. D. Rickwood and B. D. Hames, IRL Press at Oxford University Press, Oxford, 1989), respectively).

Derivatives of the invention are prepared according to conventional methods involving de novo synthesis or starting from a peptide or another derivative of the invention.

In another aspect, the present invention provides a method for treating or preventing hyperproliferative disease by interfering with the interaction or binding between p53 and MDM2 in tumor cells. The method may comprise administering an effective amount of a compound of the invention to a warm blood animal, including a human, or tumor cells containing wild type p53. The administration of the compounds of the present invention may induce cell growth arrest or apoptosis. The present invention may be used to treat disease and/or tumor cells comprising non-elevated MDM2 levels. Non elevated levels of MDM2 as used herein refers to MDM2 levels lower than those found in cells containing more than the normal copy number (2) of mdm2 or below about 10,000 molecules of MDM2 per cell as measured by ELISA and similar assays known in the art (Picksley et al., Oncogene 9, 2523–2529 (1994)).

The method of the present invention encompasses administering DNA to tumor cells and/or a warm blooded animal, including a human. DNA of the present invention encodes a product that interferes with the interaction of p53 and MDM2. DNA typically is in an expression vector, such as a retrovirus, DNA virus or plasmid into which DNA sequences necessary for expression in eukaryotic cells are properly positioned to result in expression of the DNA. The DNA sequences are designed to express high levels of the desired product in tumor cells in a form that is stable and active as exemplified by the binding element TIP 12/1 described below. The DNA may be administered to cells in vivo, ex vivo or in vitro as appropriate. The DNA may be administered encapsulated in liposomes, via microinjection or any other form known in the art to achieve efficient cellular uptake.

Administering compounds that interfere with the interaction of p53 and MDM2 by affecting the expression of MDM2 are also encompassed by the method of the present invention. Triple strand-forming and antisense oligonucleotides which bind the mdm2 gene or its mRNA and prevent transcription or translation may also be administered to tumor cells and/or a warm blooded animal, including a human, in vivo, ex vivo or in vitro. The oligonucleotides may interact with unprocessed mRNA or processed mRNA. Small molecules and peptides which specifically inhibit MDM2 expression may also be administered to cells.

In another aspect of the method of the present invention, antibodies that interfere with the interaction between p53 and MDM2 may be administered to tumor cells and/or to a warm blooded animal, including a human, facilitating cell growth arrest or apoptosis. Antibodies of the present invention interrupt p53 and MDM2 interaction, and may comprise polyclonal, monoclonal, and recombinant antibodies. Antibodies of the invention may be associated with liposomes or other means known in the art to facilitate cellular uptake. DNA encoding for the antibodies of the invention may also be administered to the cell, as described above, the antibody being delivered to the upon expression of the administered DNA.

Furthermore, the present invention relates to uses of a compound of the invention including its use in the purification of a binding partner, particularly MDM2; its use as a "lead compound" for drug development or design; its use in a method of identifying compounds which interfere with the binding of MDM2 to p53; its use in diagnosis, e.g., to measure the levels of MDM2 in blood samples in the case of leukemia or solid carcinomas, such as sarcomas or glioblastomas.

The invention relates also to pharmaceutical compositions comprising compounds of the invention, to their use in the therapeutic (including prophylactic) treatment of the hyperproliferative diseases and viral infections, to the compounds for said use and to the preparation of pharmaceutical preparations.

The pharmacologically acceptable compounds of the present invention may be used, for example, for the preparation of pharmaceutical compositions that comprise an effective amount of the active ingredient together or in admixture with a significant amount of inorganic or organic, solid or liquid, pharmaceutically acceptable carriers.

The invention provides a pharmaceutical composition that is suitable for administration to a warm-blooded animal, especially a human (or to cells or cell lines derived from a warm-blooded animal, especially a human, e.g., lymphocytes), for the treatment or prevention of (=prophylaxis against) a disease that responds to inhibition of the interaction of p53 with MDM2, comprising an amount of a peptide of the invention or a pharmaceutically acceptable derivative thereof, which is effective for said inhibition, together with at least one pharmaceutically acceptable carrier.

The pharmaceutical compositions according to the invention are those for enteral, such as nasal, rectal or oral or parenteral, such as intramuscular or intravenous, administration to warm-blooded animals (humans and animals), that comprise an effective does of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration. The invention relates also to a method of treating diseases that respond to inhibition of the interaction of MDM2 and p53, which comprises administering a prophylactically or especially therapeutically effective amount of a compound according to the invention, especially to a warm-blooded animal, for example, a human, that, on account of one of the mentioned diseases, requires such treatment. In a preferred embodiment the administered compound is a peptide or derivative of the invention.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, poly vinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of anti oxidants, for example vitamin E, β-carotene or 3,5-di-tert-butyl-4-hydroxytoluene. The alcohol component of those fatty acid esters has a maximum of 6 carbon atoms and is a mono- or polyhydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (poly oxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methyl-cellulose, hydroxypropylmethylcellulose, sodium carboxymethylcellulose and/or poly vinylpyrrolidone, and/or, if desired, disintegrates, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or poly ethylene glycol. Dragée cores are provided with suitable, optionally enteric, coatings, there being used, inter alia, concentrated sugar solutions which may comprise gum arabic, talc, poly vinylpyrrolidone, polyethylene glycol and/or titanium dioxide, or coating solutions suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added.

Dyes or pigments may be added to the tablets or dragée coatings or the capsule casings, for example for identification purposes or to indicate different doses of active ingredient.

The following Examples serve to illustrate the present invention, but should not be construed as a limitation thereof. The invention particularly relates to the specific embodiments (e.g. peptides, methods for their preparation, and assays as described in these Examples.

Abbreviations: Acrld=thioether resulting from the reaction of a Cys-sulfhydryl group in the peptide with 6-acryloyl-2-(dimethylamino)naphtalene; o/n=overnight; Aib: α-aminoisobutyric acid; $Ac_3c$: 1-amino-cyclopropane-1-carboxylic acid.

EXAMPLES

Example 1

Synthesis of N-Acylated Peptide Derivatives

The below-identified peptides are synthesized on a Milligen 9050 automated peptide synthesizer (continuous flow; Millipore, Bedford, Mass., USA), starting with an Fmoc-PAL-PEG-PS resin (see Albericio, F. et al, J. Org. Chem., 55 (1990) 3730–3743) for establishing the C-terminal carboxamide, and using chemical protocols based on the fluorenylmethoxycarbonyl chemistry (see E. Atherton and R. C. Sheppard, in Solid-Phase Peptide Synthesis—A Practical Approach, eds: R. Rickwood and B. D. Hames, IRL Press at Oxford University Press, Oxford, 1989). The required Fmoc-amino acids (3 equivalents) are incorporated using their 2,4,5-trichlorophenyl esters (single coupling) with minimum reaction times of 30 min (see 9050 Plus PepSynthesizer User's Guide, Millipore Corporation, Bedford, Mass., 1992). Side chains are protected with the following groups:

tert-butyl for aspartic acid, glutamic acid, tyrosine, serine and threonine;

tert-butyloxycarbonyl for lysine and tryptophan;

2,2,5,7,8-pentamethyl-chroman-6-sulfonyl for arginine;

trityl for histidine, cysteine, asparagine, and glutamine.

The complete peptide resins obtained after the final coupling reaction are simultaneously deprotected and cleaved by treatment with trifluoroacetic acid/water/ethanedithiol (76:4:20, v/v/v) for 3 h at room temperature. The complete peptide resins obtained after the final coupling reaction are simultaneously deprotected and cleaved by treatment with trifluoroacetic acid/water/ethanedithiol (76:4:20, v/v/v) for 3 h at room temperature. The filtrate from each cleavage reaction is precipitated in diisopropyl ether-petroleum ether (1:1, v/v) at 0° C., and the precipitates are collected by filtration. The crude compounds are dissolved in 2N AcOH/acetonitrile (1:1, v/v) to remove the $N^{in}$-carboxy group from the side chain of tryptophan. The course of the reactions is monitored by analytical reversed-phase HPLC. After 2 h at 40° C., the solutions are concentrated to dryness and the crude peptides are purified by reversed-phase medium-pressure liquid chromatography using a $C_{18}$ column eluted with an acetonitrile-water gradient containing 0.1% trifluoroacetic acid (Merck LICHROPREP RP-18, 15–25 μm bead diameter, reversed phase column material based on $C_{18}$-derivatised silicagel, Merck, Darmstadt, FRG; column length 46 cm, diameter 3.6 cm; flow rate 53.3 ml/min; detection at 215 nm). Mass spectrometric analyses (matrix-assisted laser-desorption ionization time-of-flight mass spectrometry, MALDI-TOF) reveal molecular masses within 0.1% of the expected values (positive or negative ion mode). Quantitative amino acid analyses of the final products reveal amino acid compositions within 5% of the expected values. The purity of the peptides is verified by reversed-phase analytical HPLC on a Nucleosil column (250×4.0 mm; 5 mm, 100): linear gradient over 10 min of MeCN/0.09% TFA and $H_2O$/0.1% TFA from 1:49 to 3:2; flow rate 2.0 ml/min, detection at 215 nm (HPLC System A); HPLC System B: linear gradient over 10 min of MeCN/0.09% TFA and $H_2O$/0.1% TFA from 1:49 to 1:0; flow rate 2.0 ml/min, detection at 215 nm.

The peptides are as follows:

Ac-Thr-Gly-Pro-Ala-Phe-Thr-His-Tyr-Trp-Ala-Thr-Phe-$NH_2$ (TFA salt) SEQ ID NO:18;

Mass spectral analysis (negative-ion mode): 1441.7 (calc. 1441.6, $C_{71}H_{92}N_{16}O_{17}$), $t_R^{(retention\ time)}$=8.08 rein (HPLC System A).

Ac-Met-Pro-Arg-Phe-Met-Asp-Tyr-Trp-Glu-Gly-Leu-Asn-$NH_2$ (TFA salt) SEQ ID NO:19;

Mass spectral analysis (negative-ion mode): 1598.9 (calc. 1598.9, $C_{73}H_{101}N_{18}O_{19}S_2$), $t_R$=8.82 min (HPLC System A).

Ac-Gln-Pro-Thr-Phe-Ser-Asp-Tyr-Trp-Lys-Leu-Leu-Pro-$NH_2$ (TFA salt) SEQ ID NO:20;

Mass spectral analysis (negative-ion mode): 1534.8 (calc. 1534.8, $C_{75}H_{105}N_{16}O_{19}$), $t_R$=8.73 min (HPLC System A).

Ac-Pro-Ala-Phe-Thr-His-Tyr-Trp-Pro-$NH_2$ (TFA salt) SEQ ID NO:21;

Mass spectral analysis (negative-ion mode): 1060.3 (calc. 1060.2, $C_{14}H_{67}N_{12}O_{11}$), $t_R$=8.21 min (HPLC System A).

Ac-Pro-Thr-Phe-Ser-Asp-Tyr-Trp-Pro-$NH_2$ SEQ ID NO:22

Mass spectral analysis (negative-ion mode): 1052.0 (calc. 1052.1, $C_{52}H_{63}N_{10}O_{14}$), $t_R$=7.97 (HPLC System A).

Ac-Pro-Arg-Phe-Met-Asp-Tyr-Trp-Pro-$NH_2$ (TFA salt) SEQ ID NO:23;

Mass spectral analysis (negative-ion mode): 1151.6 (calc. 1151.3, $C_{16}H_{72}N_{13}O_{12}S_1$), $t_R$=8.42 (HPLC System A).

Ac-Gln-Glu-Thr-Phe-Ser-Asp-Leu-Trp-Lys-Leu-Leu-Pro-NH$_2$ (TFA salt) (wild-type sequence) SEQ ID NO:24

Mass spectral analysis (negative-ion mode): 1517.1 (calc. 1516.8, $C_{72}H_{107}N_{16}O_{20}$), $t_R$=9.30 (HPLC System A), $t_R$=6.65 (HPLC System B)

Ac-Gln-Pro-Thr-Phe-Ser-Asp-Leu-Trp-Lys-Leu-Leu-Pro-NH$_2$ (TFA salt) SEQ ID NO:25

Mass spectral analysis (negative-ion mode): 1485.0 (calc. 1484.8, $C_{72}H_{107}N_{16}O_{18}$), $t_R$=9.32 (HPLC System A), $t_R$=6.66 (HPLC System B)

Ac-Gln-Glu-Thr-Phe-Ser-Asp-Tyr-Trp-Lys-Leu-Leu-Pro-NH$_2$ (TFA salt) SEQ ID NO:26

Mass spectral analysis (negative-ion mode): 1567.3 (calc. 1566.8, $C_{75}H_{105}N_{16}O_{21}$), $t_R$=8.55 (HPLC System A), $t_R$=6.19 (HPLC System B).

Ac-Val-Gln-Asn-Phe-Ile-Asp-Tyr-Trp-Thr-Gln-Gln-Phe-NH$_2$ SEQ ID NO:27

Mass spectral analysis (negative-ion mode): 1628.8 (calc. 1628.8, $C_{78}H_{103}N_{18}O_{21}$), $t_R$=7.03 (HPLC System A);

Ac-Ile-Asp-Arg-Ala-Pro-Thr-Phe-Arg-Asp-His-Trp-Phe-Ala-Leu-Val-NH$_2$ (TFA salt) SEQ ID NO:28

Mass spectral analysis (negative-ion mode): 1883.9 (calc. 1884.2, $C_{89}H_{128}N_{25}O_{21}$), $t_R$=8.57 min (HPLC System A)

Ac-Pro-Arg-Pro-Ala-Leu-Val-Phe-Ala-Asp-Tyr-Trp-Glu-Thr-Leu-Tyr-NH$_2$ (TFA salt) SEQ ID NO:29

Mass spectral analysis (negative-ion mode): 1881.6 (calc. 1881.2, $C_{12}H_{127}N_{20}O_{23}$), $t_R$=9.58 min (HPLC System A); $t_R$=6.88 min (HPLC System B).

Ac-Pro-Ala-Phe-Ser-Arg-Phe-Trp-Ser-Asp-Leu-Ser-Ala-Gly-Ala-His-NH$_2$ (TFA salt) SEQ ID NO:30

Title compound: Mass spectral analysis (negative-ion mode): 1688.6 (calc. 1688.9, $C_{78}H_{107}N_{22}O_{21}$), $t_R$=9.09 min (HPLC System A); $t_R$=6.48 min (HPLC System B)

If desired, the peptide derivatives contain a free N-terminal amino group. Peptides with a free N-terminal amino group include:

H-Thr-Gly-Pro-Ala-Phe-Thr-His-Tyr-Trp-Ala-Thr-Phe-NH$_2$ (TFA salt) SEQ ID NO:31

Mass spectral analysis (negative-ion mode): 1396.6 (calc. 1396.6, $C_{69}H_{87}N_{16}O_{16}$), $t_R$=7.86 min (HPLC System A).

H-Met-Pro-Arg-Phe-Met-Asp-Tyr-Trp-Glu-Gly-Leu-Asn-NH$_2$ (TFA salt) SEQ ID NO:32

Mass spectral analysis (negative-ion mode): 1556.6 (calc. 1556.8, $C_{71}H_{99}N_{18}O_{18}S_2$), $t_R$=7.92 min (HPLC System A).

Example 2

Synthesis of Cys(Acrld) Peptide Derivatives

I. Ac-Cys(Acrld)-Gly-Gln-Pro-Thr-Phe-Ser-Asp-Tyr-Trp-Lys-Leu-Leu-Pro-NH$_2$ (TFA salt) SEQ ID NO:33

Ac-Cys-Gly-Gln-Pro-Thr-Phe-Ser-Asp-Tyr-Trp-Lys-Leu-Leu-Pro-NH$_2$ (TFA salt) SEQ ID NO:34 is obtained analogously to Example 1 (Mass spectral analysis (negative-ion mode): 1694.7 (calc. 1695.0, $C_{80}H_{113}N_{18}O_{21}S_1$), $t_R$=8.39 (HPLC System A)). To a solution of Ac-Cys-Gly-Gln-Pro-Thr-Phe-Ser-Asp-Tyr-Trp-Lys-Leu-Leu-Pro-NH$_2$ (18 µmol) SEQ ID NO:34 in 20 ml of degassed phosphate buffer (pH=7.5) is added 6-acryloyl-2(dimethylamino) napthtalene (2-fold excess; Molecular Probes, Inc., Leiden, The Netherlands) dissolved in 2 ml of acetonitrile. The solution is stirred overnight at room temperature under an argon atmosphere. After completion of the reaction, 1 ml of trifluoroacetic acid is added and the solution is concentrated to dryness. The compound is purified by reversed-phase medium-pressure liquid chromatography. Title compound: Mass spectral analysis (negative-ion mode): 1920.4 (calc. 1920.3, $C_{95}H_{128}N_{19}O_{22}S_1$), $t_R$=9.20 (HPLC System A); $t_R$=6.60 (HPLC System B).

II. Ac-Cys(Acrd)-Gly-Pro-Thr-Phe-Ser-Asp-Leu-Trp-Pro-NH$_2$ (TFA salt) SEQ ID NO:35

Ac-Cys-Gly-Pro-Thr-Phe-Ser-Asp-Leu-Trp-Pro-NH$_2$ SEQ ID NO:36 is obtained analogously to Example 1 (Mass spectral analysis (negative-ion mode): 1162.0 (calc. 1162.3, $C_{54}H_{73}N_{12}O_{15}S_1$), $t_R$=8.00).

The title compound (II) is obtained analogously to the previous example (I).

Title compound: Mass spectral analysis (negative-ion mode): 1387.6 (calc. 1387.6, $C_{69}H_{88}N_{13}O_{16}S_1$), $t_R$=9.63 (HPLC System A), $t_R$=6.87 (HPLC System B).

III. Ac-Cys(Acrd)-Pro-Thr-Phe-Ser-Asp-Leu-Trp-Pro-NH$_2$ (TFA salt) SEQ ID NO:37

Ac-Cys-Pro-Thr-Phe-Ser-Asp-Leu-Trp-Pro-NH$_2$ SEQ ID NO:38 is obtained analogously to Example 1. (Mass spectral analysis (negative-ion mode): 1105.5 (calc. 1105.3, $C_{52}H_{70}N_{11}O_{14}S_1$), $t_R$=8.25 (HPLC System A).

The title compound is obtained analogously to the above example.

Title compound: Mass spectral analysis (negative-ion mode): 1330.6 (calc. 1330.6, $C_{67}H_{85}N_{12}O_{15}S_1$), $t_R$=9.82 (HPLC System A); $t_R$=7.02 (HPLC System B).

Example 3

Synthesis of Biotinylated Peptide Derivatives

Biotin-Ser-Gly-Ser-Gly-Gln-Glu-Thr-Phe-Ser-Asp-Leu-Trp-Lys-Leu-Leu-Pro-NH$_2$ (TFA salt) (wild-type sequence) SEQ ID NO:39

(+)-Biotin (3 equivalents; Fluka, Buchs, Switzerland) is coupled with N-[(dimethylamino)1H-1,2,3-triazolo[4,5-b]pyridin-1-ylmethylene]-N-methylmethan-aminium hexafluorophosphate N-oxide (3 equiv.; double coupling; PerSeptive Biosystems, Hamburg, Germany) in the presence of diisopropylethylamine (6 equiv.) Mass spectral analysis (negative-ion mode): 1989.5 (calc. 1989.3, $C_{90}H_{135}N_{22}O_{27}S_1$), $t_R$=9.02 (HPLC System A), $t_R$=6.55 (HPLC System B)

Biotin-Ser-Gly-Ser-Gly-Gln-Pro-Thr-Phe-Ser-Asp-Leu-Trp-Lys-Leu-Leu-Pro-NH$_2$ TFA salt) SEQ ID NO:40.

Mass spectral analysis (negative-ion mode): 1957.9 (calc. 1957.3, $C_{90}H_{135}N_{22}O_{25}S_1$), $t_R$=9.04 (HPLC System A), $t_R$=6.57 (HPLC System B).

Biotin-Ser-Gly-Ser-Gly-Gln-Glu-Thr-Phe-Ser-Asp-Tyr-Trp-Lys-Leu-Leu-Pro-NH$_2$ TFA salt) SEQ ID NO:41.

Mass spectral analysis (negative-ion mode): 2039.3 (calc. 2039.3, $C_{93}H_{133}N_{22}O_{28}S_1$), $t_R$=8.46 (HPLC System A).

Biotin-Ser-Met-Pro-Arg-Phe-Met-Asp-Tyr-Trp-Glu-Gly-Leu-Asn-Arg-Gln-Ile-Lys-Ile-Trp-Phe-Gln-Asn-Arg-Arg-Met-Lys-Trp-Lys-Lys-NH$_2$ (TFA salt) SEQ ID NO: 42

Mass spectral analysis (negative-ion mode): 4098.4 (calc. 4099.0, $C_{188}H_{284}N_{55}O_{41}S_4$), $t_R$=9.08 min (HPLC System A); $t_R$=6.41 min (System B). This derivative comprises a biotin label, serine as spacer, a peptide of the invention and the penetratin sequence Arg-Gln-Ile-Lys-Ile-Trp-Phe-Gln-Asn-Arg-Arg-Met-Lys-Trp-Lys-Lys SEQ ID NO:43 from the homeodomain of the Antennapedia protein (D. Derossi, J. Biol. Chem. 269, 10444–10450 (1994)).

Ac-Ala-Ala-Val-Ala-Leu-Leu-Pro-Ala-Val-Leu-Leu-Ala-
    Leu-Leu-Ala-Pro-PAla-Met-Pro-Arg-Phe-Met-Asp-
    Tyr-Trp-Glu-Gly-Leu-Asn-βAla-Lys(Biotin)-NH$_2$
    (TFA salt) SEQ ID NO:44

The peptide contains the internalization vector: Ala-Ala-Val-Ala-Leu-Leu-Pro-Ala-Val-Leu-Leu-Ala-Leu-Leu-Ala-Pro SEQ ID NO:45 (Lin et al., J. Biol. Chem. 270, 14255–14258 (1995)).

The peptide is synthesised as described in Example 1 using N$^\alpha$-Fmoc-Lys(Aloc)-OH. After the incorporation of the last residue, the side chain of lysine is selectively deprotected with tetrakis(triphenylphosphine) palladium (0) in the presence of trimethylsilylacetate and 4(trimethylsilyl) morpholine dissolved in dichloromethane. The deprotection is carried out in an argon atmosphere for 2 h at room temperature, followed by washing with dichloromethane (4×1 min), N-methylpyrrolidin-2-one (4×1 min), 0.05 M sodium diethyldithiocarbamate in DMF containing 0.5% of diisopropylethylamine (4×1 min), and N-methylpyrrolidin-2-one (4×1 min). The incorporation of (+)-biotin to the side chain of lysine is mediated by N[dimethylamino) 1H-1,2,3-triazolo [4,5-b)pyridin-1-ylmethylene]-N-methylmethanaminium hexafluorophosphate N-oxide in the presence of diisopropyl ethylamine. Title compound: Mass spectral analysis (negative-ion mode): 3593.7 (calc. 3593.4, C$_{169}$H$_{265}$N$_{40}$O$_{40}$S$_3$), t$_R$=9.15 (HPLC System B).

Example 4

Cyclic Peptide Derivatives Containing Disulphide Bond

Cyclic peptides containing a disulphide bond are synthesized from the respective cysteinyl peptides as follows: the cysteinyl peptide (20 mg; in the following referred to as starting compound) is dissolved in a 0.1 M solution of ammonium bicarbonate (20 ml). The mixture is left to stand open to atmosphere. Aliquots of the solution are removed at different times and analysed by analytical HPLC. After 24 h, the reaction mixture is concentrated to dryness. The crude compound is dissolved in water and injected directly in a medium-pressure liquid chromatography system as described above, and the title compound is obtained.

Ac-Cys-Thr-Phe-Ser-Asp-Tyr-Trp-Cys-NH$_2$ SEQ ID NO: 46 is obtained analogously to Example 1. Starting compound: Mass spectral analysis (negative-ion mode): 1064.6 (calc. 1064.2, C$_{48}$H$_{58}$N$_{10}$O$_{14}$S$_2$), t$_R$=8.15 (HPLC System A).

SEQ ID NO: 47
Ac-Cys-Thr-Phe-Ser-Asp-Tyr-Trp-Cys-NH$_2$
    S--------------------------S

Title compound: Mass spectral analysis (negative-ion mode): 1062.2 (calc. 1062.2, C$_{48}$H$_{57}$N$_{10}$O$_{14}$S$_2$), t$_R$=7.96 (HPLC System A). Ac-Cys-Ala-Phe-Thr-His-Tyr-Trp-Cys-NH$_2$ (TFA salt) SEQ ID NO:48;

Starting compound: Mass spectral analysis (negative-ion mode): 1070.0 (calc. 1070.2, C$_{50}$H$_{61}$N$_{12}$O$_{11}$S$_2$), t$_R$=8.35 (HPLC System A).

SEQ ID NO: 49
Ac-Cys-Ala-Phe-Thr-His-Tyr-Trp-Cys-NH$_2$(TFA salt)
    S--------------------------S Mass spectral analysis (positive-ion mode): 1070.4 (calc. 1070.2, C$_{50}$H$_{61}$N$_{12}$O$_{11}$S$_2$), t$_R$=8.13 min (HPLC System A).
Ac-Cys-Arg-Phe-Met-Asp-Tyr-Trp-Cys-NH$_2$ (TFA salt) SEQ ID NO:50
Starting compound: Mass spectral analysis (negative-ion mode): 1163.7 (calc. 1163.4, C$_{52}$H$_{68}$N$_{13}$O$_{12}$S$_3$) t$_R$=8.67 (HPLC System A).

SEQ ID NO: 51
Ac-Cys-Arg-Phe-Met-Asp-Tyr-Trp-Cys-NH$_2$(TFA salt)
    S--------------------------S Mass spectral analysis (negative-ion mode): 1161.1 (calc. 1161.4, C$_{52}$H$_{66}$N$_{13}$O$_{12}$S$_3$), t$_R$=8.33 min (HPLC System A).

As an alternative to cysteine, penicillamine (β,β-dimethyl-cysteine) can be used. Also, L-cysteine may be changed for D-cysteine either at the N- or C-terminus, or in both sides. Peptides containing thioether bridges are formed from starting compounds having a free cysteine residue at the C-terminus and a bromo-containing building block at the N-terminus (e.g., bromo-acetic acid). Cyclisation can be carried out on solid phase by a selective deprotection of the side chain of cysteine (Mayer, J. P. et al., Tetrahedron Lett. 361411, 7387–7390 (1995)).

Example 5

Synthesis of Lactam Peptide Derivatives

The peptide is synthesised manually on a 4-(2',4'-dimethoxyphenyl-aminomethyl)-phenoxy-resin (Novabiochem, Läufelfingen, Switzerland), employing the fluorenyl-methoxycarbonyl strategy. Fmoc-removal is with piperidine/dimethylacetamide (1:4, v/v; 6×2 min), followed by washing with methanol (3×1 min), N-methylpyrrolidin-2-one (2×1 min), methanol (3×1 min), and N-methylpyrrolidin-2-one (3×2 min). Amino acid side chains are protected with the following groups: tert-butyl for threonine, serine, aspartic acid and tyrosine; 2,2,5,7,8-pentamethyl-chroman-6-sulfonyl for arginine; tert-butyloxycarbonyl for tryptophan; ally for glutamic acid; and allyloxycarbonyl for lysine. The required Fmoc-derivatives of tryptophan, tyrosine, threonine, serine, aspartic acid, arginine, methionine, phenylalanine and alanine are incorporated using their 2,4,5-trichlorophenyl esters (2 equiv.) in the presence of 1-hydroxybenzotriazole (2 equiv.) and diisopropylethylamine (0.75 equiv.). The incorporation of N$^\alpha$-Fmoc-Lys (Aloc)-OH (2 equiv.; PerSeptive Biosystems, Hamburg, Germany) and N$^\alpha$-Fmoc-Glu(OAll)-OH (2 equiv.; Millipore, Bedford, Mass., U.S.A.) is accomplished with benzotriazole-1-yl-oxy-tris-(dimethylamino)-phosphonium-hexafluorophosphate/1hydroxybenzotriazole (1:1; 2 equiv.) in the presence of diisopropylethylamine (4 equiv.)

Coupling is achieved by first dissolving the Fmoc-amino acid, diisopropylethylamine, and the coupling reagent in N-methylpyrrolidin-2-one, then waiting 3 min for preactivation, adding the mixture to the resin, and finally shaking for at least 45 min. After the incorporation of the last residue, the side chains of glutamic acid and lysine are selectively deprotected with tetrakis(triphenylphosphine) palladium (0) (Fluka, Buchs, Switzerland) in the presence of trimethylsilylacetate and 4-(trimethylsilyl)morpholine dissolved in dichloromethane. The deprotection is carried out in an argon atmosphere for 2 h at room temperature, followed by washing with dichloromethane (4×1 min), N-methylpyrrolidin-2-one (4×1 min), 0.05 M sodium diethyldithiocarbamate in DMF containing 0.5% of diisopropylethylamine (4×1 min), and N-methylpyrrolidin-2-one (4×1 min). Intramolecular cyclisation on the solid support is accomplished with benzotriazole-1-yl-oxy-tris(dimethylamino)-phosphonium-hexafluorophosphate/1-hydroxybenzotriazole (1:1; 6 equiv.; double coupling) in the presence of diisopropylethylamine (12 equiv.). The complete peptide resin obtained after the cyclisation step is simultaneously deprotected and cleaved by treatment with trifluoroacetic acid/water/ethanedithiol (76:4:20, v/v/v) for 3 h at room temperature. The filtrate is precipitated in diisopropyl ether-petroleum ether (1:1, v/v) at 0° C., and the precipitate is collected by filtration. The crude compound is dissolved in 2N AcOH/acetonitrile (1:1, v/v) to remove the $N^{in}$-carboxy group from the side chain of tryptophan. The courses of the reactions are monitored by analytical reversed-phase HPLC. After 2 h at 40° C., the solution is concentrated to dryness and the crude peptide is purified by medium-pressure liquid chromatography as described above.

SEQ ID NO: 52

Ac-Glu-Thr-Phe-Ser-Asp-Tyr-Trp-Lys-NH₂(TFA salt)

------------CO-NH------------

Mass spectral analysis (negative-ion mode): 1097.5 (calc. 1097.2, $C_{53}H_{66}N_{11}O_{15}$). $t_R$=7.49 min (HPLC System A).

SEQ ID NO: 53

Ac-Glu-Arg-Phe-Met-Asp-Tyr-Trp-Lys-NH₂(TFA salt)

------------CO-NH------------

Mass spectral analysis (negative-ion mode): 1196.7 (calc. 1196.4, $C_{57}H_{75}N_{14}O_{13}S_1$), $t_R$=8.09 min (HPLC System A).

As an alternative to glutamic acid, it is possible to use aspartic acid. As an alternative to lysine, ornithine or diaminobutyric acid may be used. As an alternative to side—side cyclisation, it is possible to make a lactam between the side chain of aspartic acid or glutamic acid at the C-terminus and the α-amino group of the N-terminal amino acid. This approach can also be expanded to β-amino acids (e.g., β-alanine).

The following peptides are synthesised as described in Example 1:

Ac-Phe-Met-Aib-Tyr-Trp-Aib-Gly-Leu-NH₂ SEQ ID NO:54

Title compound: Mass spectral analysis (negative-ion mode): 1026.5 (calc. 1026.3, $C_{52}H_{69}N_{10}O_{10}S_1$), $t_R$=7.81 (HPLC System B).

Ac-Arg-Phe-Met-Aib-Tyr-Trp-Aib-Gly-Leu-NH₂ SEQ ID NO:55

Title compound: Mass spectral analysis (negative-ion mode): 1182.6 (calc. 11182.4, $C_{58}H_{81}N_{14}O_{11}S_1$), $t_R$=7.09 (HPLC System B).

Ac-Arg-Phe-Met-Aib-Tyr-Trp-Glu-Ac₃c-Leu-NH₂ (TFA salt) SEQ ID NO:56

Title compound: Mass spectral analysis (negative-ion mode): 1252.7 (calc. 1252.5, $C_{61}H_{83}N_{14}O_{13}S_1$), $t_R$=6.91 (HPLC System B).

Ac-Phe-Met-Aib-Tyr-Trp-Aib-Ac₃c-Leu-NH₂ SEQ ID NO:57

Title compound: Mass spectral analysis (negative-ion mode): 1052.3 (calc. 1052.3, $C_{54}H_{71}N_{10}O_{10}S_1$), $t_R$=8.03 (HPLC System B).

Ac-Phe-Met-Aib-Tyr-Trp-Glu-Ac₃c-Leu-NH₂ SEQ ID NO:58

The peptide is synthesised as described in Example 5. The incorporation of $N^α$-Fmoc-1-amino-cyclopropane-1-carboxylic acid (2 equiv.) is carried out with benzotriazole-1-yl-oxy-tris-(dimethylamino)-phosphonium hexafluorophosphate/N-hydroxybenzotriazole (1:1; 2 equiv.) in the presence of diisopropylethylamine (5 equiv.). $N^α$-Fmoc-aminoisobutyric acid (2 equiv.) is coupled with benzotriazole-1-yl-oxy-tris-(dimethylamino)-phosphonium hexa-fluorophosphate/N-hydroxybenzo-triazole (1:1; 2 equiv.; first coupling) and N-[(dimethyl-amino)-1 H-1,2,3-triazolo-[4,5-b]pyridin-1-ylmethylene]-N-methylmethanaminium hexa fluoro-phosphate N-oxide (2 equiv.; second coupling) in the presence of diisopropyl ethylamine (5 equiv.). A second coupling for glutamic acid and methionine (2 equiv.) is performed with N-[(dimethylamino)-1H-1,2,3-triazolo-[4,5-b]pyridin-1-ylmethylene]-N-methylmethanaminium hexafluorophosphate N-oxide (2 equiv.; second coupling) in the presence of diisopropyl-ethylamine (5 equiv.). The complete peptide resin obtained after the final coupling reaction is simultaneously deprotected and cleaved by treatment with trifluoro acetic acid/H₂O (95:5, v/v) for 3 h at room temperature. The filtrate from the cleavage reaction is precipitated in diisopropyl ether/petroleum ether (1:1, v/v, 0° C.), and the precipitate collected by filtration.

The crude peptide is purified as described in Example 1.

Title compound: Mass spectral analysis (negative-ion mode): 1096.4 (calc. 1096.3, $C_{55}H_{71}N_{10}O_{12}S_1$), $t_R$=7.62 (HPLC System B).

The starting material is prepared as follows:

a) $N^α$-Fmoc-1-amino-cyclopropane-1-carboxylic acid

The title compound is synthesised starting from 1-amino-cyclopropane-1-carboxylic acid (Fluka, Buchs, Switzerland) according to a procedure known in the art (see E. Atherton et al., in: Solid-Phase Peptide Synthesis—A Practical Approach; D. Rickwood and B. D. Hames, IRL Press at Oxford University Press, Oxford, 1989): $R_f$=0.44 (chloroform:methanol:water:acetic acid=850:130:15:5, v/v/v/v). m.p.=223–225° C.

Example 6

Synthesis of Peptide Fragment Derivatives

The below identified peptide fragment derivatives are sythesised analogously to the method described in Example 1 above:

Ac-Arg-Phe-Met-Asp-Tyr-Trp-Glu-Gly-Leu-NH₂ (TFA salt) SEQ ID NO: 59

Mass spectral analysis (negative-ion mode): 1256.4 (calc. 1256.4, $C_{59}H_{79}N_{14}O_{15}S_1$), $t_R$=8.69 (HPLC System A), $t_R$=7.02 (HPLC System B).

Ac-Phe-Met-Asp-Tyr-Trp-Glu-Gly-Leu-NH₂ SEQ ID NO: 60

Mass spectral analysis (negative-ion mode): 1100.5 (calc. 1100.3, $C_{53}H_{67}N_{10}O_{14}S_1$), $t_R$=9.38 (HPLC System A), $t_R$=6.76 (HPLC System B).

Ac-Phe-Met-Aib-Tyr-Trp-Glu-Gly-Leu-NH$_2$ SEQ ID NO: 61

Mass spectral analysis (negative-ion mode): 1070.4 (calc. 1070.3, $C_{53}H_{69}N_{10}O_{12}S_1$), $t_R$=7.14 (HPLC System B).

Ac-Phe-Met-Asp-Tyr-Trp-Aib-Gly-Leu-NH$_2$ SEQ ID NO: 62

Mass spectral analysis (negative-ion mode): 1056.2 (calc. 1056.2, $C_{12}H_{67}N_{10}O_{12}S_1$), $t_R$=7.07 (HPLC System B).

Example 7

Fluorescence Assay

The DNA region of the mdm2 gene encoding the first 188 amino acids of the protein is obtained by Polymerase Chain Reaction (PCR) amplification of the mdm2 gene. The oligonucleotides used for PCR are designed such that a BamHI restriction site is introduced at the 5' extremity of the gene and an EcoRI restriction site at its 3' end. The PCR fragments digested by BamHI and EcoRI are ligated with a BamHI/EcoRI cleaved pGEX-2T vector. The resulting vector comprises a fusion gene consisting of the full length sequence of glutathione-S-transferase of *S. japonicum*, a linker sequence, and the N-terminal 188 amino acids of HDM2, in the 5' to 3' order. The complete gene is sequenced on both strands and the recombinant plasmid is introduced into *E. coli* strain BL21 (Novagen).

Glutathione-S-transferase protein (for control experiments) is obtained from *E. coli* strain BL21 (Novagen) transformed with pGEX-2T plasmid.

The test compound (c=50 nM), e.g. a fluorogenic peptide described in Example 4, is titrated with different amounts of the GST-hdm2 protein (c=0, 50 nM, 200 nM, and 300 nM). The fluorescence emission spectra ($\lambda_{ex}$=370 nm) are recorded in a spectrofluorophotometer at 20° C. The instrument setting during the titration is identical so that the fluorescence intensities in the presence or absence of the GST-hdm2 protein can be compared. A stock solution of the fluorogenic peptide is prepared in a PBS buffer (pH=7.6) containing 10% glycerol, 1% Triton 100, 50 mM NaCl and BSA (1 mg/ml). The peptide (c=50 nM) is incubated for 30 min with different amounts of the GST-hdm2 protein. After this time, the fluorescence emission spectrum is recorded. The addition of the GST-hdm2 protein to the solution containing the fluorogenic peptide results in an increase in the emission fluorescence of the fluorogenic peptide at 530 nm. The fluorescence emission spectra of the GST-hdm2 protein (c=50–300 nM) is identical to the fluorescence emission spectra of the buffer, so the protein does not contribute to the observed increase in emission fluorescence.

This assay is applicable to the detection of specific interactions of peptides or low molecular weight compounds with the MDM2 protein. In addition, it allows accurate kinetic measurements in solution.

Example 8

Identification of MDM2 Binding Peptides by Phage Display

In deviation from the previous definition, in the following Examples "hdm2" refers to the human double minute gene2 and the corresponding protein.

Phage Selection

The phage libraries used in this study display random peptide sequences of six, twelve or fifteen amino acid residues at the N-terminus of the minor coat protein III. These libraries are provided by George Smith (University of Missouri, 6 and 15mer) and William Dower (Affymax Research Institute, 12mer). In a biopanning procedure library samples are screened on solid phase GST-hdm2 (hdm2 comprising amino acids 1–188). Polystyrene petri dishes (Falcon 3001) are coated with 5 µg/ml GST-hdm2 or DO-1 (monoclonal anti-p53 antibody) overnight at 4° C. in a humidity chamber. Unbound material is washed off with 2.5 ml PBS and the dishes are blocked with 2 ml TBST-M (150 mM NaCl, 50 mM Tris-HCI, pH 7.5, 0.1% (v/v) Tween20, 5% (w/v) low fat milk powder) for 1 h at 4° C. The petri dishes are washed three times with 2.5 ml PBS and 500 µl phage suspension containing $1 \times 10^{11}$ (6 and 12mer libraries) or $7.5 \times 10^{12}$ TU (transforming units) is added and allowed to bind for 3 h at 4° C. After washing ten times with 2.5 ml TBST, bound phages are eluted with 400 µl elution buffer (0.1 N HCl-glycine pH2.2, 1 mg/ml BSA) for 20 min. The eluates are neutralized with 24 µl 2M Tris base and used to infect 2.5 ml log-phase *E. coli* K91 cells (50 min; 37° C.). The whole suspension is transferred into 50 ml Falcon tubes with 10 ml 2xYT medium containing 20 µg/ml tetracycline (2xYT, Tet) and incubated for 24 hours at 37° C. with shaking. The cultures are spun to remove the bacteria and the phage particles are purified from the supernatant by PEG precipitation. The phage pellets are resuspended in 1 ml TBS and aliquots are used for a second round of biopanning which is carried out as for the first with the following modifications:

100 µl amplified phage ($2 \times 10^{11}$ TU) are reacted with GST-hdm2, MBP-hdm2 or DO-1 which has been absorbed in wells of a 96-well PVC assay plate at a concentration of 5 µg/ml. Amplified and purified phages from this round of biopanning are tested in an ELISA on the proteins used for their selection. For single clone screening *E. coli* K91 cells are infected with appropriate phage dilutions and spread on LB agar with 20 µg/ml tetracycline. Single colonies are transfered to wells of a 96-well tissue culture plate containing 200 µl 2xYT medium with 20 µg/ml tetracycline per well. Phage supernatant is collected for ELISA screening after a 24 hour incubation at 37° C. with shaking. ELISA positive clones are grown up as 2 ml bacterial cultures in 2xYT medium with 20 µg/ml tetracycline for 24 hours. Phage are PEG precipitated and redissolved in 200 µl TBS buffer. Phage DNA is extracted with phenol/chloroform and ethanol precipitated. The DNA pellet is redissolved in 10 µl water and used as template for sequencing (Sequenase).

Phage Elisa

Solid Phase hdm2

PVC assay plates are coated with 100 µl antigen (GST-hdm2, MBP-hdm2, GST, MBP, or DO-1) at 5 µg/ml in PBS overnight at 4° C. and blocked with 200 µl PBST-M (PBS, containing 5% (w/v) fat-free dried milk and 0.1%.(v/v) Tween 20) for one hour at room temperature. 100 µl phage suspension (supernatant or PEG concentrated phage) is diluted in PBST-M and added for three hours at 4° C. Bound phages are reacted with 100 µl HRP-labelled sheep anti-M13 antibody (Pharmacia) for one hour at room temperature followed by substrate development with 100 µl TMB/H$_2$O2 (0.1 mg/ml TMB, 0.3% H$_2$O$_2$ in 0.1 M Na-acetate, pH 6.0) for 15 min. The reaction is stopped by adding 100 µl 1M sulphuric acid to the substrate and the absorbance is measured at 450 nm. All washings between the incubation steps are done with tap water.

Solution Phase hdm2

GST-, MBP-, TRX-hdm2 or baculovirus produced mdm2 (Sf9 cell extract) diluted in PBST-M are reacted in solution with hdm2- or GST-binding phage overnight at 4° C. Simultaneously, ELISA plates are coated with 100 µl Rabbit anti-mouse antibodies (DAKO, Z0259) 1:1000 in 0.1 M NaHCO₃, pH 9.6. The plates are blocked as usual and incubated with monoclonal anti-mdm2 antibodies (hybridoma supernatant 1:5 diluted in PBST-M) for one hour. For the titration ELISA, purified SMP14 (8 µg/ml in PBS) is used to coat the plate directly. In either case, the pre-incubated phage-hdm2 samples are transferred to the coated and blocked plate and incubated for two hours at room temperature. Bound phages are detected as described.

Results

Phage pools which have been recovered from two rounds of biopanning on solid phase GST- and MBP-hdm2 or DO-1 using samples of 6, 12, or 15mer phage display libraries are screened in ELISAs for antigen binding. Phage from 12 and 15mer libraries selected twice with GST-hdm2 or once with GST-hdm2 followed by MBP-hdm2 clearly bind to GST-hdm2, whereas the 6mer pool is completely negative. On the other hand, monoclonal anti-p53 antibody DO-1 is able to select phages from all three libraries proving the integrity of the 6mer library.

To determine whether phages specific for hdm2 are selected, the phage pools are tested against MBP-hdm2, GST and MBP. Both, 12 and 15mer pools contain hdm2 binding phages (positive for MBP-hdm2, but negative for MBP alone). In addition, 15mer phages twice biopanned with GST-hdm2 (GST/GST-hdm2) are strongly selected for GST-binders. In the 15mer pool which is panned on MBP-hdm2 in the second round (GST/MBP-hdm2) the anti-GST signal is reduced, probably because GST is no longer present as a selecting antigen. GST does not pull out any phage from the 12mer library. Single phage clones are grown from 12 and 15mer pools and tested for GST, GST-hdm2 and MBP-hdm2 binding. Many clones are clearly positive with GST-hdm2 and MBP-hdm2. Phage clones from the 12 and 15mer pools which are shown to be positive with GST- and MBP-hdm2 are selected for further analysis. Phage DNA is extracted from each clone and the nucleotide inserts are sequenced. From 28 clones 6 unique insert sequences are obtained (amino acid sequences given in single letter code):

sequences contain the phenylalanine (F) and Tryptophan (W), and 4 out of 6 the aspartic acid (D) and leucine (L) found in the same position in the mdm2 motif. A strong selection for tyrosine (Y) and proline (P) in the phage sequences is not met by corresponding residues in the p53 sequence, although 2 successive prolines are found further upstream of the mdm2 binding site.

Further experiments are designed to evaluate the specificity of the hdm2-phage interaction and to prove that p53 and hdm2 phage bind to the same region on hdm2. For these experiment clones BB2/BB11 (GST binding control phage) and BB3/BB10 (hdm2 phage) are chosen. Phages are pre-incubated in solution with GST-hdm2, MBP-hdm2 or TRX-hdm2 and the phage-hdm2 complexes are transferred to wells which contain different monoclonal anti-mdm2 antibodies bound to the solid phase via anti-mouse antibodies. Bound phages are detected. As expected, GST-phages are able to bind only to GST-hdm2. All three anti-mdm2 antibodies used (SMP 14, 4B2, 3G5) are able to bind to hdm2 complexed with GST-phage. Antibody SMP14 is commercially available and described in Picksley et al., Oncogene 9, 2523–2529 (1994) incorporated by reference above. Antibodies 3G5 and 4B2 are described in Chen, J. et al., Mol. Cell Bio., vol. 13, 4107–4114 (1993) also incorporated herein by reference in its entirety. On the other hand, the hdm2-phage recognizes all three hdm2 fusion proteins including TRX-hdm2 never used for the phage selection (biopanning). The hdm2-phage complexes are efficiently pulled down by SMP14 and 4B2, but 3G5 is hardly able to bind to these complexes. It has been shown that mdm2-p53 complexes cannot be bound by 3G5, probably because the epitope of this antibody lies within the p53 binding domain of mdm2. Another experiment shows that hdm2-phages but not GSTphages are able to inhibit the interaction between hdm2 and TIP. TIP is thioredoxin with the mdm2 binding sequence of p53 inserted into its active site. In order to estimate the relative affinities of the different phage clones towards hdm2, a dilution series of GST-hdm2 is offered in solution to a fixed amount of phages. Phage-hdm2 complexes are pulled down by solid phase SMP14 and bound phages are detected. All phage clones tested show a very similar strong binding to GST-hdm2 with a half-maximal binding concentration of 0.5 to 10 nM GST-hdm2, dependent on the hdm2 preparation used. Experiments with baculovirus produced mdm2 (Sf9 cell extract) prove that the phage clones selected with hdm2 are able to bind to its mouse homologue as well.

```
mdm2 binding site on human p53   PLSQETFSD L WKLLPENNV   SEQ ID NO: 1
phage clone 12/1                     MPRFMDYWEGLN         SEQ ID NO: 6
phage clone 12/2                     VQNFIDYWTQQF         SEQ ID NO: 63
phage clone 12/5                     TGPAFTGYWATF         SEQ ID NO: 64
phage clone 15/1                     IDRAPTFRDHWFALV      SEQ ID NO: 65
phage clone 15/5                     PRPALVFADYWETLY      SEQ ID NO: 8
phage clone BB3                      PAFSRFWSADLSAGAH     SEQ ID NO: 66
phage consensus                      PXFXDYWXXL           SEQ ID NO: 3
```

Aligning the corresponding amino acid sequences to each other reveals the phage consensus sequence P X F X D Y W X X L SEQ ID NO:3. It shows similarity to the known mdm2 binding motif on p53, T F S D L W SEQ ID NO:83 (amino acid residues 18–23 of human p53; Picksley et al., Oncogene 9, 2523–2529 (1994) which reference is incorporated herein by reference in its entirety. All phage The phage sequences and a consensus sequence are produced as free peptides and tested for their relative capacity to block the interaction of MDM2 with p53 in three different ELISA formats. The new consensus sequence and some of the phage derived peptides show a remarkable increase in specific activity over the wild type p53 peptide sequence.

Materials and Methods for Protein Expression

1. Thioredoxin(Thio)-Fusions

The clones are produced using the Invitrogen-Expression system. Using Bluescript containing the hdm2 gene as a template, PCR is carried out with the following primers (5'-3'):

START2 primer SEQ ID NO:67: gcg gat ccg atg gtg agg agc agg caa atg

STOP1 (to N221) SEQ ID NO:68: gcc tgc agc cta att cga tgg cgt ccc tgt aga

STOP2 (full length) SEQ ID NO:69: gc ctg cag cta ggg gaa ata agt tag cac aat

STOPS (to D294) SEQ ID NO:70: gc ctg cag cta atc ttc ttc aaa tga atc tgt

START3 primer (from D294) SEQ ID NO:71: ggg gat cct gaa att tcc tta gct gac.

The resulting PCR products are cloned into pCR II (TA cloning kit, Invitrogen). The resulting plasmids are cleaved with BamH1 and PstI. The products are ligated into the BamH1/PstI cleaved pTrxFus. The plasmid is introduced into E. coli G1724. The following clones are obtained:

1. clone 1/8 Thio-MVRSRQ-MI . . . N221

2. clone 3/8 Thio-MVRSRQ-MI . . . D294

3. clone 2/7 Thio MVRSRQ-MI . . . C478

2. Maltose Binding Protein (MBP)-Fusion

The PCR product is obtained using the STOP1 primer described above with START1 SEQ ID NO:72:

gc gga tcc atg gtg agc agc agg caa atg

It is again cloned into pCR II. The plasmid is cut with BamH1 and PstI. The products are ligated into BamH1/PstI cleaved pMALc2 (New England Biolabs). The plasmids are then introduced into E. coli INV(F' cells (One ShotTMcompetent cell kit, Invitrogen). Clone 4 (MBP-MVRSRQ-M1 . . . N221) is obtained.

3. GST-Fusion Protein

A plasmid containing wild type hdm2 is used as a template in PCR. The primers are designed such that a BamH1 site is introduced into the 5' end and a EcoR1 site into the 3' end of the gene. The PCR products are digested and ligated into pGEX-2T (Pharmacia). The plasmid is then introduced into E. coli BL21 cells.

Protein Expression:

1. Thioredoxin-Fusionproteins

Cells are grown in RM medium (1×M9 salts, 2% Casamino acids, 1% glycerol, 1 mM MgCl$_2$, 100 g/ml ampicillin) overnight at 30° C. They are then inoculated into fresh Induction medium (1×M9 salts, 0.2% Casamino acids, 0.5% glucose, 1 mM MgCl$_2$, 100 g/ml ampicillin to a dilution of 1/20. Cells are then grown to an OD of 0.25 to 0.5 at 30° C. The culture is transferred to 37° C. and induced with L-Tryptophan at a final concentration of 100 g/ml. After 3 h cells are harvested by centrifugation. The pellets are resuspended in ice cold 20 mM Tris/HCl, pH 8, 2.5 mM EDTA with protease inhibitors (1 mM PMSF, 1 mM benzamidine, leupeptin, approtinin and pepstatin at 10 g/ml each. The cells are lysed by sonication, shock freezing, quick thawing. The cycle is repeated two more times. The lysate is then centrifuged at 4000 rpm for 15 min at 4° C. The supernatant is used.

2. Maltose Binding Protein-Fusions

Cells are grown in rich Medium with glucose and ampicillin (10 g tryptone, 5 g yeast extract, 5 g NaCl, 2 g glucose and 100 g/ml ampicillin to an OD of 0.5. They are then induced with IPTG at a final concentration of 0.3 mM. Incubation is continued at 37° C. for another 2 h. Cells are harvested by centrifugation and resuspended in column buffer (½oth of original volume, 20 mM Tris-HCl, pH 7.4; 200 mM NaCl; 1 mM EDTA; 1 mM DTT plus protease inhibitors as mentioned above. Cells are frozen over night at −20° C. They are thawed in cold water, sonicated on ice in short pulses of 6×10 seconds and spun at 9000 rpm for 30 min at 4° C. The supernatant is diluted 1/5 with column buffer and loaded on an amylose resin (New England Biolabs, 15 ml, prepared in column buffer). Elution is carried out with column buffer +10 mM Maltose. Active fractions are pooled, concentrated and desalted on a 10 DG column (BioRad). They are stored in 50 mM Tris/Hcl pH 7.4, 50 mM NaCl, 20% glycerol, 1 m M DTT.

3. GST-hdm2 (1–188)

Bacteria cultures are grown to OD 0.8. They are cooled to RT and induced with 1 mM IPTG, then grown for 4 h at 27° C. Cells are harvested and pellets flash frozen in liquid nitrogen. Pellets are resuspended in ice cold buffer A (0.5 M NaCl, 2.7 mM KCl, 10 mM Na$_2$HPO$_4$, 1.8 mM KH$_2$PO$_4$, 1 mM PMSF, 1 mM EDTA, 10 mM 2-mercaptoethanol, pH 7.3). They are lysed by a French press or alternatively by sonication. After centrifugation the soluble fraction is loaded onto a glutathione sepharose 4B column (Pharmacia) equilibrated with buffer A. The protein is then eluted with buffer B (50 mM Tris/HCl, 10 mM reduced glutathione, 0.5 M NaCl, 1 mM EDTA. 1 mM PMSF or benzamidine, 10 mM 2mercaptoethanol or 1 mM DTT, pH 8.0.) Active fractions are desalted on Sephadex G25 or 10 DG (BioRad) preequilibrated with buffer C (50 mM Tris/HCl, 50 mM NaCl, 20% glycerol, 10 mM 2-mercaptoethanol or 1 mM DTT, 0.1% Triton x-100, pH 7.6). The protein is used for Elisas or further purified on a Mono Q column (Pharmacia) preequilibrated with buffer C. The protein is eluted with a linear gradient of buffer C containing 1 M NaCl. The fractions containing fusionprotein are pooled, concentrated (Centricon 30), flash frozen in liquid nitrogen and stored at −70° C.

ELISAs

Three different Elisas are employed to analyze the interaction between hdm2 and p53. They are named according to the reagent which is used to coat the Elisa plates. All Elisas are carried out at 4° C.

1. Elisa P2

P2 is a biotinylated peptide consisting of 18 amino acids of the Terminal part of p53, namely: Biotin-S-G-S-G-E-P-P-L-S-Q-E-T-F-S-D-L-W-K-L-L-P-E SEQ ID NO:73. Plates are incubated overnight with 10 µg/ml streptavidin at 37° C. They are blocked with 2% BSA in PBS for 1 h. Peptide is applied at 5 µg/ml in blocking solution for 1 h. A second blocking step is carried out with 5% milk, 0.1% Tween20 in PBS (blocking solution2) for a minimum of 10 min. Hdm2 fusion proteins are diluted in blocking solution2 and applied for 1 h. Bound hdm2 is detected with SMP 14 hybridoma cell supernaiant diluted 1/2 in block solution2. HRP-anti-mouse IgG (DAKO) is used as second antibody. Washing between incubations is carried out 6 times with tap water.

2. Elisa TIP

TIP is thioredoxin which has additional amino acids inserted into its active site. These are derived from the N-terminus of p53 and are the following:

P-P-L-S-Q-E-T-F-S-D-L-W-K-L-L-P-E-N SEQ ID NO:74.

The following are used

P1 SEQ ID NO: 75: 5' gt ccg cct ctg agt cag gaa aca ttt tca gac cta tgg aaa cta ctt cct gaa aacg3'

P2 SEQ ID NO: 76: 5' g acc gtt ttc agg aag tag ttt cca tag gtc tga aaa atg ttt cct gac tca gag gcg 3'

10 ng of each P1 and P2 are phosphorylated using PNK and annealed for 1 h at 37° C. The vector pTRX (InVitrogen) is cleaved with RsrII and dephosphorylated. After ligation the plasmids are introduced into *E. coli* 1724 cells.

Plasmid containing bacteria are grown in RM medium at 30° C. and induced with L-Trp as described earlier. A soluble lysate is made by freeze-thaw-sonication cycles. This lysate is then heat shocked at 80° C. for 10 min. The soluble fraction is used to coat Elisa-plates at a concentration of 40 µg/ml in PBS o/n. Plates are blocked in blocking solution2 for 1 h. Incubation with hdm2 fusionproteins and detection is carried out as described for Elisa P2.

3. Elisa hdm2

Plates are coated with 2.6 µg/ml GST-hdm2(1–188) in PBS at 4° C. o/n. They are blocked in blocking solution 2 for 1 h. Full length p53, lysozyme lysate from *E. coli*, purified on heparin-sepharose is applied in blocking solution2 with 10% glycerol and 10 mM DTT for 1 h. Binding is established with mAb 421 and HRP coupled anti mouse IgG.

HRP activity is measured using TMB. For inhibition Elisas inhibitors are preincubated with either hdm2-fusionproteins or p53 for 15 min before the mixture is transferred to the plate. Peptide inhibitors are dissolved in DMSO.

Example 9

Purification of p53 D30

The human wild type p53 gene is used as a template for PCR to obtain the gene fragment encoding for residues 1 to 362 of the 393 amino acids of natural (human) p53 (p53D30). The oligonucleotides used for PCR are designed such that a NdeI restriction site is introduced at the 5' end and a BamHI site at the 3' end. The PCR fragments digested by NdeI and BamHI are ligated with a NdeI/BamHI cleaved pET-3a plasmid. The complete gene is sequenced and the expression plasmid is introduced into *E. coli* strain BL21 (DE3)pLysS (Novagen).

For protein expression bacteria cultures are inoculated by a 100-fold diluted overnight culture and grown in Luria Broth medium in the presence of 100 µg ampicillin/ml at 37° C. to $OD_{600}$=0.8. The cultures are then cooled on ice to room temperature, induced with 1 mM isopropyl-D-thiogalactopyranoside and grown for four additional hours at 27° C. The cells are then harvested by centrifugation and the pellets flash frozen in liquid nitrogen and stored at −70° C.

The cell pellets containing the p53D30 protein are resuspended in ice cold buffer D (50 mM 4-(2-hydroxyethyl)-piperazine-ethane-sulfonic acid (Hepes.NaOH), 10% (v/v) glycerol, 0.1 mM EDTA, 0.1% (v/v) Triton X-100, 5 mM 1,4-dithio-DL-threitol (DTT), 1 mM PMSF–pH=7.6) and lysed with a French press at 1000 psi. After centrifugation, the soluble fraction is loaded onto a HiTrap Heparin column (Pharmacia Biotech) preequilibrated at 4° C. with buffer D. The column is first washed with buffer D containing 22% buffer E (50 mM Hepes.NaOH, 1 M KCl, 10% (v/v) glycerol–pH=7.6) and p53D30 is eluted with a linear gradient to 100% buffer E. The fractions containing p53D30 are pooled and loaded onto a HiTrap metal chelation column (Pharmacia Biotech) charged with nickel and preequilibrated at 4° C. with buffer F (50 mM Hepes.NaOH, 0.5 M KCl, 10% (v/v) glycerol–pH=7.6). After washing the column with buffer F containing 20% buffer G (50 mM Hepes.NaOH, 0.5 M KCl, 10 (v/v) glycerol, 0.1 M immidazole–pH=7.6), p53D30 is eluted with 45% buffer G. 50 mM 2-mercaptoethanol and 1 mM $ZnCl_2$ are added to the solution and the protein is dialysed at 4° C. against 50 mM Hepes.NaOH, 0.5 M KCl, 20% (v/v) glycerol, 50 mM 2-mercaptoethanol, 1 mM $ZnCl_2$–pH=7.6. p53D30 is concentrated to 1 mg/ml (Amicon 30 kDa cut off membrane), flash frozen in liquid nitrogen and stored at −70° C.

Protein Analysis

The purity of the protein preparation is evaluated by gel scanning (Schimadzu CS-930) on a SDS-PAGE (Laemmli, U.K. (1970) Nature, 227, 680–385) stained with Coomassie blue. Protein concentration is determined according to Bradford, M. B. (1976) Anal. Biochem., 72, 248–254).

Example 10

To improve the intracellular stability and facilitate cellular uptake of the peptides described in examples 1 to 9, peptide binding elements may be constructed in which the peptides of the present invention are presented on the active site of *Escherichia coli* thioredoxin. The pTrx vector (Invitrogen) is cleaved with restriction enzyme RsrII. Oligomers, corresponding to the peptide identified on clone 12/1, described in example 8 above, and wild type p53 sequences are phosphorylated, annealed and then ligated into the cleaved pTrx vector.

The following oligomers may be use to produce a binding element (TIP wt) comprising a p53 wild type peptide insert:

5'-3'

```
GTCCGCCTCTGAGTCAGGAAACATTTTCAGACCTATGGAAACTACTTCCTGA SEQ ID NO:77, and 5'-3'

AAACG

GACCGTTTTCAGGAAGTAGTTTCCATAGGTCTGAAAATGTTTCCTGACTCAG SEQ ID NO:78

AGGCG
```

The following oligomers may be used to produce a binding element (TIP 12/1) comprising the peptide insert of clone 12/1 described in example 8.

5'-3':

```
GTCCGCCTCTGAGTATGCCTCGTTTTATGGATTATTGGGAGGGTCTTAATGA   SEQ ID NO:79 and 5'-3-
AAACG
GACCGTTTTCATTAAGACCCTCCCAATAATCCATAAAACGAGGCATACTCTC   SEQ ID NO:80.
AGAGGCG
```

E. Coli 1724 cells are transformed with the resulting plasmids as well as pTrx which may act as a negative control binding element (Trx) comprising thioredoxin without a peptide insert. The cultures may be grown in RM medium (1×M9 salts, 2% Casamino acids, 1% glycerol, 1 mM $MgCl_2$, 100 g/ml ampicillin) overnight at 30° C. The cultures are inoculated into fresh induction medium (1×M9 salts, 0.2% Casamino acids, 0.5% glucose, 1 mM $MgCl_2$, 100 g/ml ampicillin to a dilution of 1/20) and grown to an Optical Density (OD) of 0.25 to 0.5 at 30° C. The culture is transferred to 37° C. and induced with L-Tryptophan at a final concentration of 100 g/ml. After 3 hours to 4 hours cells are harvested by centrifugation. The pellets are resuspended in ice cold 20 mM Tris/HCl, pH 8, 2.5 mM EDTA with protease inhibitors 1 mM PMSF, 1 mM benzamidine, leupeptin, approtinin and pepstatin at 10 g/ml each. The cells are lysed by shock freezing, thawing and sonicating. The cycle is repeated two more times. The soluble lysate is then centrifuged at 10000 g for 20 min at 4° C. Heat shock lysates are obtained by resuspending petllets to an OD of 100 and then treating at 80° C. for 10 minutes followed by centrifugation at 10,000 g for 20 min.

Purification of soluble extracts is carried out by loading clear soluble lysates onto an Ion exchange Q50 column (BioRad) and eluting with a linear gradient of 0.05M–1MKCL in 50 mMTris/HCL pH7.8, 0.1% Triton X-100, 10% glycerol and 50 mMKCL.

Active fractions may be identified on dot blots with an anti-thioredoxin antibody available from Invitrogen. The active fractions may then be concentrated using Centriprep 3 filters (Amicon) and loaded unto a G100 column (Pharmacia) which has been preequilibrated with 30 mM HEPES, pH 8.0, 500 mM KCL, 0.1% Triton X100, and 10% glycerol. Following elution, active fractions may be pooled, concentrated and dialyzed against PBS.

For expression in mammalian cells, the complete thioredoxin coding region with peptide insertions (TIP wt, and TIP 12/1) or without peptide inserts (Trx) may be PCR amplified using standard PCR reagents and conditions known in the art and the following primers:

```
5'-3': CGGGATCCACCATGGGCGATAAAATTATTCACCTG   SEQ ID NO:81 and
5'-3': CTCGACGCTAACCTGGCCTAGGGAATTCC         SEQ ID NO:82.
```

The resulting PCR products may be cleaved with BamH1 and Eco RI and ligated into BamH1 and EcoR1 cleaved pcDNA3. pcDNA3 (Promega) is a vector having a CMV promoter for driving expression of TIP wt, TIP 12/1 and Trx in mammalian cells. The plasmids may be amplified in E. coli as known in the art. Plasmid DNA encoding for TIP 12/1, TIP wt and Trx may be purified using a Quiagent purification system or phenol/chloroform precipitation.

Antibodies or DNA encoding the described binding elements may be microinjected into Vrn.6 cells, a transformed rat thyroid epithelial cell line and T22 cells, a mouse prostrate derived cell line both cell lines being stably transfected with pRGC ΔFosLacz, a p53 responsive β-galactosidase reporter. Production of the Vrn.6 cell line and the pRGCΔFos-Lacz reporter are known in the art. Blaydes, J. P. et al., (1997), Oncogene, vol 14, in press; and Hupp, T. R et al. (1995) Cell, vol. 83, 237–245 hereby incorporated by reference in its entirety. Vrn.6 tolerate high levels of wild type p53 and overexpress MDM2 at a protein level. T22 cells typically contain low levels of p53 and mdm2.

For microinjection, cells may be seeded into tissue culture dishes and grown to 60–70% confluence. Microinjection may be performed using an Eppendorfer microinjection system (Microinjector 5242, Micromanipulator 5170) mounted to an Axiovert light microscope (Zeiss) having a heated stage.

Purified mouse monoclonal antibodies 3G5 and 4B2 may be injected intranuclearly and cytoplasmicly in PBS at a concentration of 1.3 mg/ml. Plasmid DNA encoding for TIP 12/1, TIP wt and Trx may be injected intronuclearly in water at a concentration of 0.25 mg 7 ml. Following microinjection, fresh medium may be added to the cell cultures and the cultures further incubated for 24 hours.

To detect β-galactosidase activity, cells may be washed with PBS and fixed with 2% formaldehyde, /0.2% glutaraldehyde in PBS for 5 minutes on ice. The cells may be washed again and overlaid with X-gal (0.25 mg/ml) in a reaction mix (5 mM potassium ferricyanide, 2 mM magnesium chloride in PBS). Cells may then be incubated at 37° C. for 16 hours after which they may be observed for blue stained cells indicating a positive response.

Results:

In Vm.6 cells, having overexpressed MDM2, a positive response was observed when 3G5 antibody or TIP were injected intranuclearly. There was not a positive response when Trx was injected intranuclearly. 3G5 binds mdm2 within the p53 binding pocket thereby blocking p53-DMD2 association (Böttinger et al., 1997).

In T22 cells, a low level p53 and mdm2 containing cell line, a strong positive response was observed when 3G5 and TIP 12/1 were injected. A positive but lower level response was observed when TIPwt was injected. No response was observed when 4B2 antibody or Trx were injected. 4B2 is an anti MDM2 antibody that targets an epitope outside the p53 binding pocket on MDM2.

DNA encoding the described binding elements TIP 12/1, TIP wt and Trx and the pRGCΔFosLacZ reporter may be transiently transfected into the following three different cell types, OSA cells, a human osteosarcoma cell line, U2-Os cells, another osteosarcoma cell line, and MCF-7 cells, a breast cancer cell line containing wild type p53. The OSA cell line contains a highly elevated mdm2 level due to gene amplification (Florence et al., 1994). The U2-OS cell line has no gene amplification for mdm2 but has elevated levels of dmd2-mRNA (Florence et al. 1994). The MCF-7 cell line contains heterogenously expressed low levels of wild type p53 and no reported mdm2 elevation.

For transient transfection and reporter induction, cells are seeded into 6 well plates at $1.5 \times 10^6$ cell per well. They are grown to a density of 80% confluence and transfected using different Lipophilic reagents such Lipofectin and Lipofectamin from Promega or Dosper and Dotap from Boehringer. 2.5 μg of TIP encoding plasmid DNA, 1 μg RGCΔFosLacZ DNA and 5–10 μg of lipophili reagent according to manufacturer instructions are mixed in serum free medium and applied to the cells. Two to four hours after transfection, complete medium is added. Forty-eight hours after transfection β-galactosidase activity is measured using DPRG (Boehringer) as a substrate. Cells are scraped into PBS and centrifuged. Pellets from each well are dissolved in 50 μl of Reporter Lysis buffer (Promega) and incubated on ice for 15 minutes. Soluble Lysates are incubated with CPRG in 100 mM phosphate buffer, pH 7.0. Optical Density at 595 nm is measured 1 to 24 hours later.

Results: Surprisingly, most induction of the p53 reporter is achieved by TIP12/1 in MCF-7 cells and in U2-OS cells. Lower induction is observed in TIP 12/1 transfected OSA cells. Transfection of the control plasmid alone induces a low level response of p53 dependent transcriptional activation in MCF-7 and U2-OS cells but is almost completely absent in OSA cells.

T22 cells, U2-Os cells, OSA cells and SAOS 2 cells may be grown in in Dulbeccor's modified Eagle medium (DMEM) supplemented with 10% Fetal Calf Serum. Additionally, for T22 cells 1 mg/ml of the antibiotic G418 may be added. Vrn. 6 cells are grown as is known in the art, previously described by Blaydes et al., 1997.

The invention claimed is:

1. An isolated peptide which binds to a DM2 protein, which peptide comprises no more than 15 amino acids, and comprises an amino acid motif comprising at least the eight consecutive amino acids from F to $R_4$ of the formula $R_1$-X-F-X-$R_2$-$R_3$-W-X-X-$R_4$ (SEQ ID NO: 4)

wherein
$R_1$ is a proline (P), leucine (L), glutamic acid (E), cysteine (C) or glutamine (Q),
X stands for any natural amino acid,
$R_2$ is arginine (R), histidine (H), or aspartic acid (D),
$R_3$ is histidine (H), phenylalanine (F) or tyrosine (Y),
$R_4$ is phenylalanine (F), glutamine (Q) or leucine (L); and
F is phenylalanine and W is tryptophan,
and inhibits the binding of said DM2 protein to a p53 protein.

2. The peptide according to claim 1 wherein the peptide binds to human DM2 (HDM2).

3. The peptide according to claim 1, which is coupled to a biotin moiety.

4. The peptide according to claim 1, which is a cyclic peptide.

5. The peptide according to claim 1, which is a cyclic lactam.

6. The peptide according to claim 1 which comprises a disulfide bond.

7. The peptide according to claim 1 which comprises an amino acid motif selected from the group consisting of M-P-R-F-M-D-Y-W-E-G-L-N (SEQ ID NO: 6), Q-P-T-F-S-D-Y-W-K-L-L-P (SEQ ID NO: 7), and P-X-F-X-D-Y-W-X-X-L (SEQ ID NO: 8).

8. An isolated peptide which comprises eight amino acids according to the formula

F-X2-R2-R3-W-X3-X4-R4 (SEQ ID NO: 10)

wherein R2 is arginine (R), histidine (H), or aspartic acid (D);
R3 is histidine (H), phenylalanine (F), or tyrosine (Y);
R4 is phenylalanine (F), glutamine (Q) or leucine (L);

X2 is methionine (M), isoleucine (I), threonine (T), arginine (R), alanine (A) or serine (S);
X3 is glutamic acid (E), threonine (T), alanine (A), phenylalanine (F) or serine (S); and
X4 is glycine (G), glutamine (Q), threonine (T), alanine (A) or aspartic acid (D).

9. The peptide according to claim 8 comprising an amino acid motif of the formula

X1-F-X2-R2-R3-W-X3-X4-R4 (SEQ ID NO: 11)

wherein
R2 is arginine (R), histidine (H), or aspartic acid (D);
R3 is histidine (H), phenylalanine (F) or tyrosine (Y);
R4 is phenylalanine (F), glutamine (Q) or leucine (L);
X1 is arginine (R), asparagine (N), alanine (A), threonine (T), or valine (V);
X2 is methionine (M), isoleucine (I), threonine (T), arginine (R), alanine (A), or serine (S);
X3 is glutamic acid (E), threonine (T), alanine (A), phenylalanine (F), or serine (S); and
X4 is glycine (G), glutamine (Q), threonine (T), alanine (A), or aspartic acid (D).

10. The peptide according to claim 1, wherein R2 is aspartic acid (D).

11. The peptide according to claim 8, wherein at least one of R2, X2, X3, and X4 is defined as follows: R2 is aspartic acid (D), X2 is methionine (M), X3 is glutamic acid (E), and X4 is glycine (G).

12. The peptide according to claim 9, wherein at least one of R2, X1, X2, X3, and X4 is defined as follows: R2 is aspartic acid (D), X1 is arginine (R), X2 is methionine (M), X3 is glutamic acid (E), and X4 is glycine (G).

13. A method for inhibiting the in vitro binding of a DM2 protein to a p53 protein comprising contacting said DM2 protein with a peptide in vitro, which peptide comprises an amino acid motif comprising at least eight consecutive amino acids of the formula $R_1$-X-F-X-$R_2$-$R_3$-W-X-X-$R_4$ (SEQ ID NO: 4)

wherein $R_1$ is a proline (P), leucine (L), glutamic acid (E), cysteine (C) or glutamine (Q), X stands for any natural amino acid, $R_2$ is arginine (R), histidine (H), or aspartic acid (D), $R_3$ is histidine (H), phenylalanine (F) or tyrosine (Y), $R_4$ is phenylalanine (F), glutamine (Q) or leucine (L); and F is phenylalanine and W is tryptophan, and inhibits the binding of said DM2 protein to a p53 protein.

14. The method of claim 13 wherein R2 is aspartic acid (D).

15. A composition comprising an isolated peptide, which peptide comprises an amino acid motif comprising at least eight consecutive amino acids of the formula $R_1$-X-F-X-$R_2$-$R_3$-W-X-X-$R_4$ (SEQ ID NO: 4)

wherein $R_1$ is a proline (P), leucine (L), glutamic acid (E), cysteine (C) or glutamine (Q), X stands for any natural amino acid, $R_2$ is arginine (R), histidine (H), or aspartic acid (D), $R_3$ is histidine (H), phenylalanine (F) or tyrosine (Y), $R_4$ is phenylalanine (F), glutamine (Q) or leucine (L); and F is phenylalanine and W is tryptophan, and inhibits the binding of said DM2 protein to a p53 protein, in admixture with at least one pharmaceutically acceptable carrier.

* * * * *